US009777050B2

(12) United States Patent
Zlotkin et al.

(10) Patent No.: US 9,777,050 B2
(45) Date of Patent: *Oct. 3, 2017

(54) PEPTIDES AND COMPOSITIONS FOR PREVENTION OF CELL ADHESION AND METHODS OF USING SAME

(71) Applicant: Tel Hashomer Medical Research, Infrastructure and Services Ltd., Tel Hashomer (IL)

(72) Inventors: Amir Zlotkin, Tel Hashomer (IL); Hen Kestenboim, Tel Hashomer (IL)

(73) Assignee: TEL HASHOMER MEDICAL RESEARCH, INFRASTRUCTURE AND SERVICES LTD., Tel Hashomer (IL)

(*) Notice: Subject to any disclaimer, the term of this patent is extended or adjusted under 35 U.S.C. 154(b) by 0 days.

This patent is subject to a terminal disclaimer.

(21) Appl. No.: 14/708,014

(22) Filed: May 8, 2015

(65) Prior Publication Data

US 2015/0315253 A1    Nov. 5, 2015

Related U.S. Application Data

(63) Continuation of application No. 13/120,049, filed as application No. PCT/IB2009/006926 on Sep. 23, 2009, now Pat. No. 9,029,318.

(60) Provisional application No. 61/136,673, filed on Sep. 24, 2008.

(51) Int. Cl.

| | |
|---|---|
| C07K 14/435 | (2006.01) |
| A61L 27/22 | (2006.01) |
| A61L 27/34 | (2006.01) |
| A61L 29/04 | (2006.01) |
| A61L 29/08 | (2006.01) |
| A61L 29/16 | (2006.01) |
| A61L 31/04 | (2006.01) |
| A61L 31/10 | (2006.01) |
| A61L 31/16 | (2006.01) |
| C02F 1/50 | (2006.01) |
| C07K 7/06 | (2006.01) |
| C07K 7/08 | (2006.01) |
| C07K 14/415 | (2006.01) |
| C07K 14/46 | (2006.01) |
| C09D 5/16 | (2006.01) |
| C02F 3/34 | (2006.01) |

(52) U.S. Cl.
CPC ...... *C07K 14/43595* (2013.01); *A61L 27/227* (2013.01); *A61L 27/34* (2013.01); *A61L 29/048* (2013.01); *A61L 29/085* (2013.01); *A61L 29/16* (2013.01); *A61L 31/047* (2013.01); *A61L 31/10* (2013.01); *A61L 31/16* (2013.01); *C02F 1/50* (2013.01); *C07K 7/06* (2013.01); *C07K 7/08* (2013.01); *C07K 14/415* (2013.01); *C07K 14/461* (2013.01); *C09D 5/1625* (2013.01); *C02F 3/34* (2013.01); *C02F 2303/20* (2013.01)

(58) Field of Classification Search
None
See application file for complete search history.

(56) References Cited

U.S. PATENT DOCUMENTS

| | | |
|---|---|---|
| 7,189,351 B2 | 3/2007 | Levin et al. |
| 2003/0103912 A1 | 6/2003 | Levin et al. |
| 2004/0172684 A1 | 9/2004 | Kovalic et al. |

FOREIGN PATENT DOCUMENTS

| | | |
|---|---|---|
| CN | 1356910 A | 7/2002 |
| CN | 101111221 A | 1/2008 |
| JP | 2005-520807 A | 7/2005 |
| JP | 2010-540431 | 12/2010 |
| WO | WO-03/057708 | 7/2003 |
| WO | WO 03/059359 A1 | 7/2003 |
| WO | WO 2004/022751 A1 | 3/2004 |
| WO | WO 2005/121778 A2 | 12/2005 |
| WO | WO 2007089272 A2 | 8/2007 |
| WO | WO 2009/037714 A2 | 3/2009 |

OTHER PUBLICATIONS

BLAST search of YDYNWY (retrieved from http://blast.ncbi.nlm.nih.gov/Blast.cgi on May 5, 2016, 19 pages).*
Uniprot entry for Q19XU3 (retrieved from http://www.uniprot.org/uniprot/Q19XU3 on Aug. 28, 2014, 2 pages).*
NCBI (retrieved from http://www.ncbi.nlm.nih.gov/protein/4TSQ_A on Aug. 26, 2016, 2 pages).*
Mechaly et al. ('Structural insights into the oligomerization and architecture of eukaryotic membrane pore-forming toxins' Structure v19 Feb. 9, 2001 pp. 181-191).*
The Communication received in the related European Patent Application No. 09740951.0, dated Jan. 20, 2012.
The Written Opinion and Search Report received in the corresponding Singapore Patent Application No. 201101836-3, dated Apr. 4, 2013.
Balban, et al., "Use of the Quorum-Sensing Inhibitor RNAII-Inhibiting Peptide to Prevent Biofilm Formation In Vivo by Drug-Resistant *Staphylococcus epidermidis*", *JID*, 2003: 187, pp. 625-630.

(Continued)

*Primary Examiner* — Karlheinz R Skowronek
*Assistant Examiner* — Ronald Niebauer
(74) *Attorney, Agent, or Firm* — Foley & Lardner LLP

(57) ABSTRACT

Compositions comprising an isolated peptide, which may for example optionally comprise a sequence selected from the group consisting of YDYNWY (SEQ ID NO: 1), YDYNLY (SEQ ID NO: 2), FDYNFY (SEQ ID NO: 3), FDYNLY (SEQ ID NO: 4), FDYNWY (SEQ ID NO: 5), YDWNLY (SEQ ID NO: 6), YDWHLY (SEQ ID NO: 7), and WDYNLY (SEQ ID NO: 8), extracted from organisms such as aquatic organisms and moss or any other sequence described herein, and methods of using same, including for treatment of or prevention of formation of microbial biofilms and against adhesion of a cell to a surface.

5 Claims, 18 Drawing Sheets

(56) References Cited

OTHER PUBLICATIONS

Bernbom, et al., "Bacterial adhesion to stainless steel is reduced by aqueous fish extract coating", *Biofilms*, 2006, 3, pp. 25-36.

Cuypers, et al., "Jellyfish and other cnidarian envenomations cause pain by affecting TRPV1 channels", *FEBS Letters*, 2006, 580, pp. 5728-5732.

Macek, et al., "Polypeptide cytolytic toxins from sea anemones (*Actiniaria*)", *FEMS Microbiology Immunology*, 1992, 105, pp. 121-130.

Fleming EA (The isolation and characterization of novel mycobacteriophages May 2004 University of Tennessee Honors.

Database UniProt [Online] Accession No. A4ANN9, last modified May 29, 2013.

Database UniProt [Online] Accession No. A6LV00, last modified May 29, 2013.

Database UniProt [Online] Accession No. A6P0V6, last modified Apr. 3, 2013.

Database UniProt [Online] Accession No. A9TTZ8, last modified May 29, 2013.

Database UniProt [Online] Accession No. A9V9E9, last modified May 29, 2013.

Database UniProt [Online] Accession No. P81662, last modified Jun. 26, 2013.

Database UniProt [Online] Accession No. Q9ADR0, last modified Jan. 9, 2013.

Office Action received in corresponding JP 2011-527422 dated Oct. 9, 2013.

Elena V Klyshko et al., "Isolation, properties and partial amino acid sequence of a new actinoporin from the sea anemone *Radianthus macrodactylus*", TOXICON, vol. 44, No. 3, Sep. 1, 2004, pp. 315-324, XP055188337, ISSN: 0041-0101, DOI: 10.1016/j.toxicon. 2004.06.006.

Huerta V et al., "Primary structure of two cytolysin isoforms from Stichodactyla helianthus differing in their hemolytic activity", TOXICON, Elmsford, NY, US, vol. 39, No. 8, Aug. 1, 2001, pp. 1253-1256, XP027272836, ISSN: 0041-0101.

International Preliminary Report on Patentability and Written Opinion mailed Apr. 7, 2011 in PCT/IB2009/006926.

International Search Report in PCT/IB2009/006926, mailed Mar. 19, 2010.

Kristan, K., et al; Pore Formation by Equinatoxin, A Eukaryotic Pore-forming Toxin, Requires a Flexible N-terminal Region and a Stable β-Sandwich; The Journal of Biological Chemistry; vol. 279, No. 45, Nov. 5, 2004; pp. 46509-46517.

Kristan, K., et al.; 1TZQ: Crystal structure of the equinatoxin II 8-69 double cysteine mutant; Worldwide Protein Data Bank Full wwPDB X-ray Structure Validation Report, Jul. 17, 2008; 10 pages.

Simpson, R.J., et al.; Tenebrosin-C; NCBI Accession No. P61915.1; Jun. 10, 2008; 2 pages.

* cited by examiner

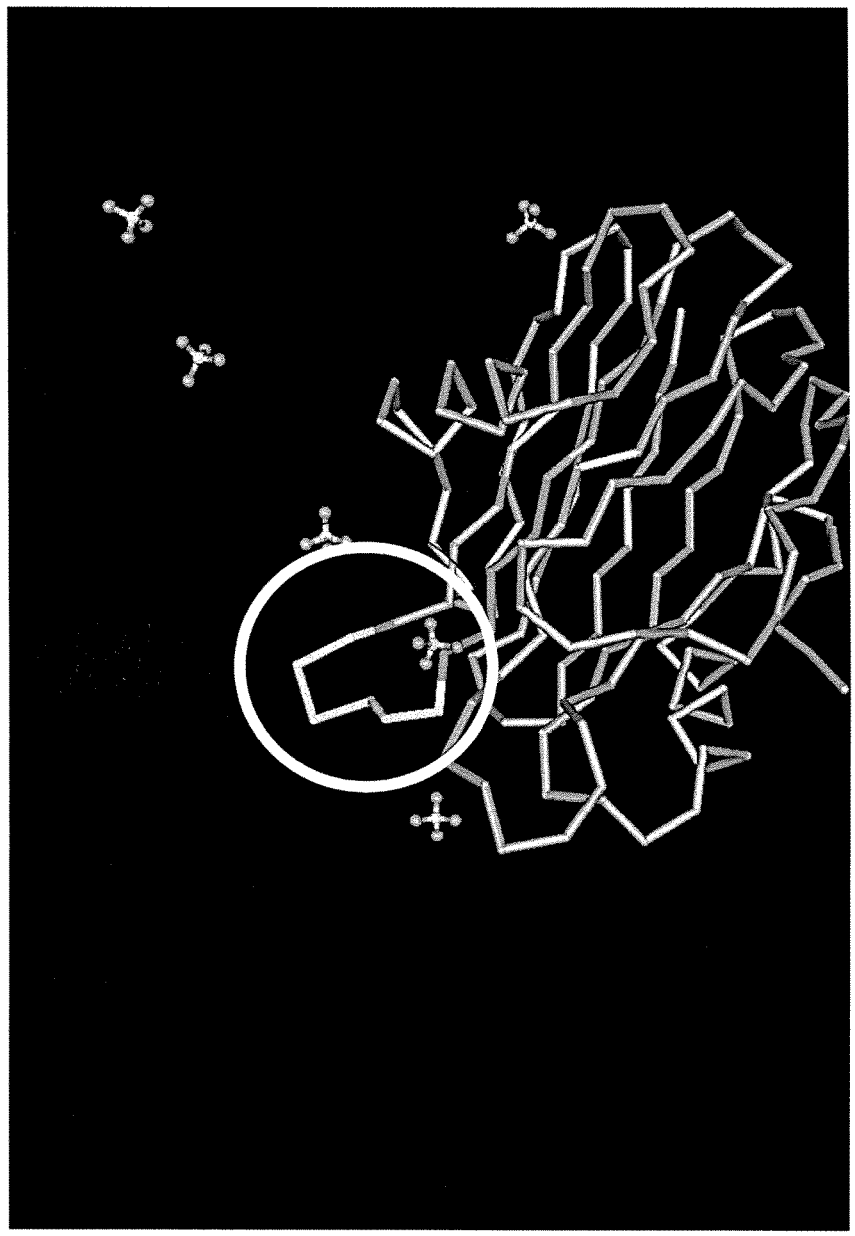
Figure 1: 1GWY Chain A, Crystal Structure Of The Water-Soluble State Of The Pore-Forming Cytolysin Sticholysin Ii

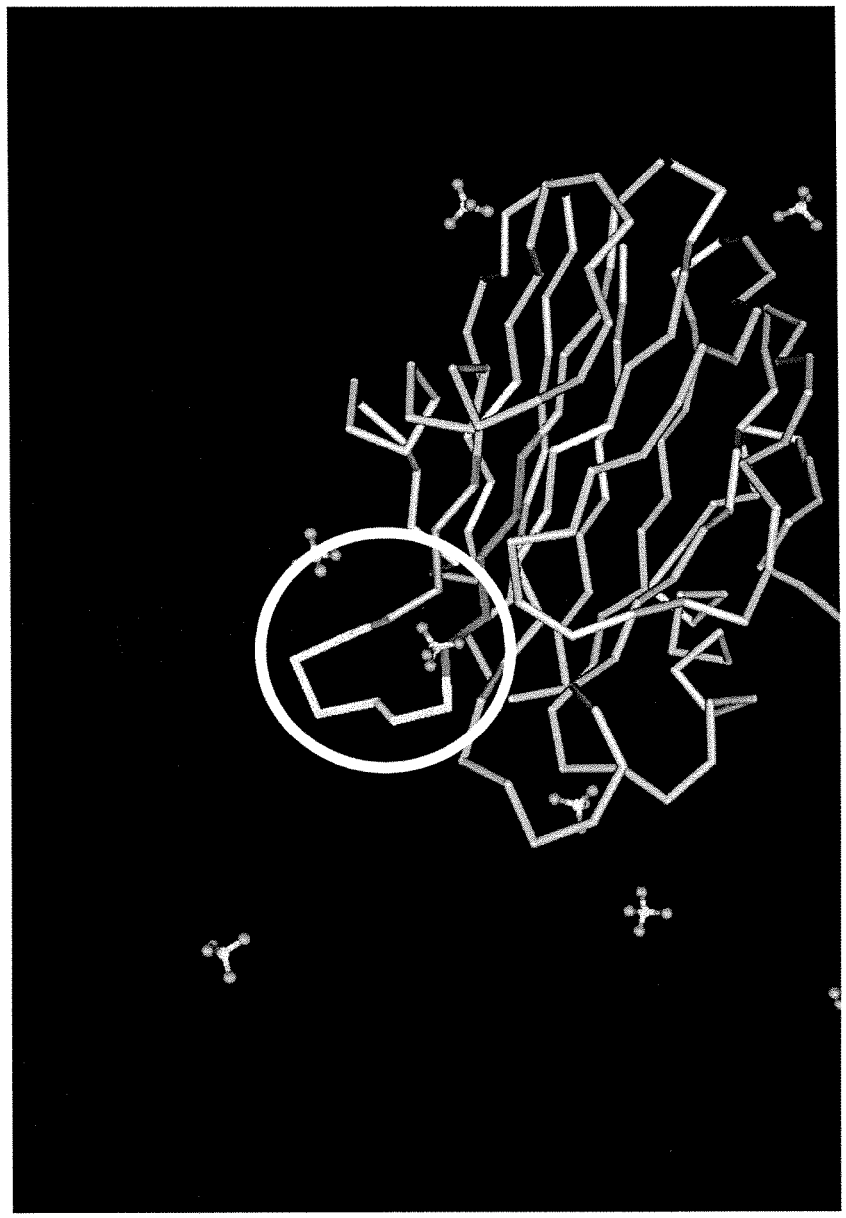
Figure 2: 1GWY Chain B, Crystal Structure Of The Water-Soluble State Of The Pore-Forming Cytolysin Sticholysin Ii

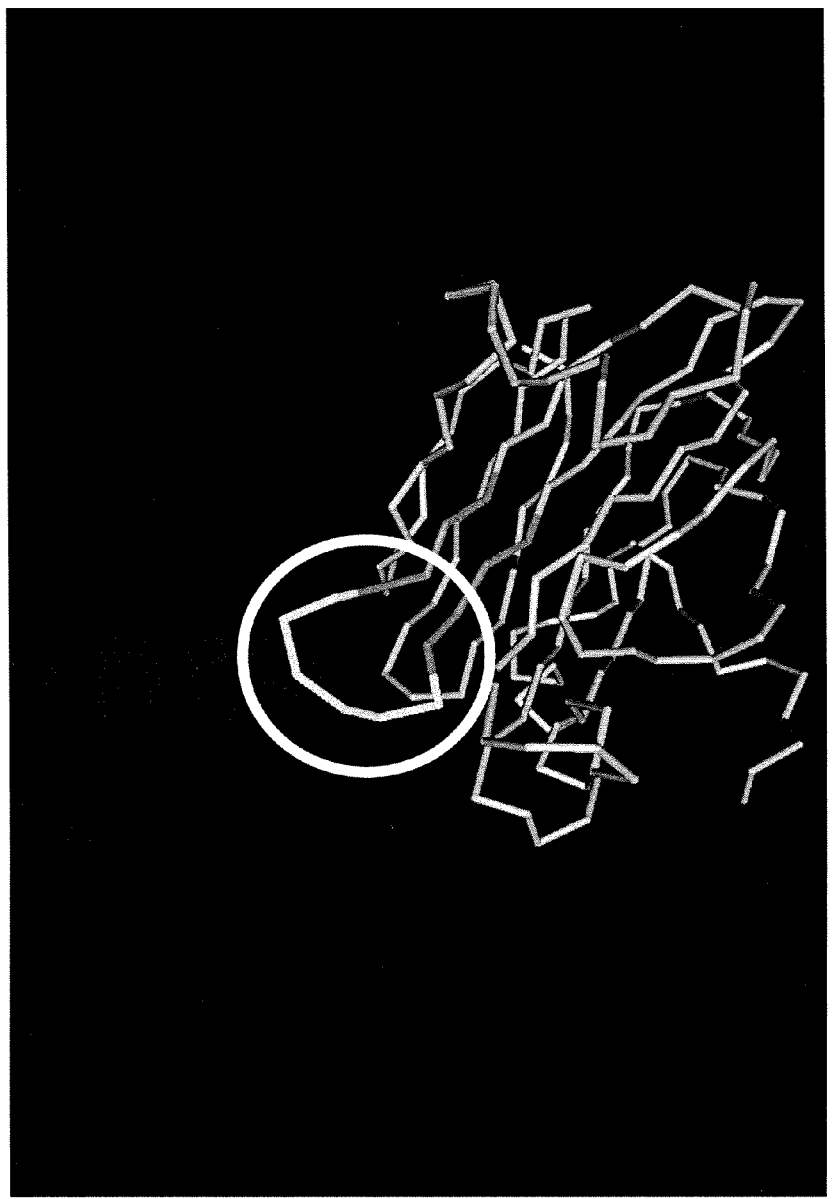
Figure 3: 1KD6 Chain A, Solution Structure Of The Eukaryotic Pore-Forming Cytolysin Equinatoxin Ii Figure 4: 1TZQ Chain A, Crystal Structure Of The Equinatoxin Ii 8-69 Double Cysteine Mutant

Prevention of *Acinetobacter Baumannii* (clinical isolate) biofilm formation

Prevention of Actinetobacter baumannii biofilm formation by Actinia equina fractions Prevention of biofilm formation by fraction 13**

Scheme 1. General structure of the cyclic lead with emulsifier arm

SEQUENCE LISTING

```
<160> NUMBER OF SEQ ID NOS: 62

<210> SEQ ID NO 1
<211> LENGTH: 6
<212> TYPE: PRT
<213> ORGANISM: Unknown
<220> FEATURE:
<223> OTHER INFORMATION: Description of Unknown: Aquatic organism or
      moss sequence

<400> SEQUENCE: 1

Tyr Asp Tyr Asn Trp Tyr
1               5

<210> SEQ ID NO 2
```

```
<211> LENGTH: 6
<212> TYPE: PRT
<213> ORGANISM: Unknown
<220> FEATURE:
<223> OTHER INFORMATION: Description of Unknown: Aquatic organism or
      moss sequence

<400> SEQUENCE: 2

Tyr Asp Tyr Asn Leu Tyr
1               5

<210> SEQ ID NO 3
<211> LENGTH: 6
<212> TYPE: PRT
<213> ORGANISM: Unknown
<220> FEATURE:
<223> OTHER INFORMATION: Description of Unknown: Aquatic organism or
      moss sequence

<400> SEQUENCE: 3

Phe Asp Tyr Asn Phe Tyr
1               5

<210> SEQ ID NO 4
<211> LENGTH: 6
<212> TYPE: PRT
<213> ORGANISM: Unknown
<220> FEATURE:
<223> OTHER INFORMATION: Description of Unknown: Aquatic organism or
      moss sequence

<400> SEQUENCE: 4

Phe Asp Tyr Asn Leu Tyr
1               5

<210> SEQ ID NO 5
<211> LENGTH: 6
<212> TYPE: PRT
<213> ORGANISM: Unknown
<220> FEATURE:
<223> OTHER INFORMATION: Description of Unknown: Aquatic organism or
      moss sequence

<400> SEQUENCE: 5

Phe Asp Tyr Asn Trp Tyr
1               5

<210> SEQ ID NO 6
<211> LENGTH: 6
<212> TYPE: PRT
<213> ORGANISM: Unknown
<220> FEATURE:
<223> OTHER INFORMATION: Description of Unknown: Aquatic organism or
      moss sequence

<400> SEQUENCE: 6

Tyr Asp Trp Asn Leu Tyr
1               5

<210> SEQ ID NO 7
<211> LENGTH: 6
<212> TYPE: PRT
<213> ORGANISM: Unknown
<220> FEATURE:
<223> OTHER INFORMATION: Description of Unknown: Aquatic organism or
      moss sequence

<400> SEQUENCE: 7
```

```
Tyr Asp Trp His Leu Tyr
1               5

<210> SEQ ID NO 8
<211> LENGTH: 6
<212> TYPE: PRT
<213> ORGANISM: Unknown
<220> FEATURE:
<223> OTHER INFORMATION: Description of Unknown: Aquatic organism or
      moss sequence

<400> SEQUENCE: 8

Trp Asp Tyr Asn Leu Tyr
1               5

<210> SEQ ID NO 9
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 9

Leu Phe Ser Val Pro Tyr Asp Tyr Asn Trp Tyr Ser Asn Trp Trp
1               5                   10                  15

<210> SEQ ID NO 10
<211> LENGTH: 14
<212> TYPE: PRT
<213> ORGANISM: Unknown
<220> FEATURE:
<223> OTHER INFORMATION: Description of Unknown: Peptide
      sequence

<400> SEQUENCE: 10

Phe Ser Val Pro Tyr Asp Tyr Asn Leu Tyr Ser Asn Trp Trp
1               5                   10

<210> SEQ ID NO 11
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 11

Met Phe Ser Val Pro Phe Asp Tyr Asn Phe Tyr Ser Asn Trp Trp
1               5                   10                  15

<210> SEQ ID NO 12
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 12

Met Phe Ser Val Pro Phe Asp Tyr Asn Leu Tyr Ser Asn Trp Trp
1               5                   10                  15

<210> SEQ ID NO 13
<211> LENGTH: 15
<212> TYPE: PRT
<213> ORGANISM: Unknown
<220> FEATURE:
```

```
<223> OTHER INFORMATION: Description of Unknown: Peptide
      sequence

<400> SEQUENCE: 13

Met Phe Ser Val Pro Phe Asp Tyr Asn Leu Tyr Thr Asn Trp Trp
1               5                   10                  15

<210> SEQ ID NO 14
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 14

Met Trp Ser Val Pro Phe Asp Tyr Asn Leu Tyr Ser Asn Trp Trp
1               5                   10                  15

<210> SEQ ID NO 15
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 15

Met Phe Ser Val Pro Trp Asp Tyr Asn Leu Tyr Lys Asn Trp Phe
1               5                   10                  15

<210> SEQ ID NO 16
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 16

Met Phe Ser Val Pro Phe Asp Tyr Asn Leu Tyr Lys Asn Trp Leu
1               5                   10                  15

<210> SEQ ID NO 17
<211> LENGTH: 16
<212> TYPE: PRT
<213> ORGANISM: Unknown
<220> FEATURE:
<223> OTHER INFORMATION: Description of Unknown: Peptide
      sequence

<400> SEQUENCE: 17

Met Phe Ser Val Pro Phe Phe Asp Tyr Asn Trp Tyr Ser Asn Trp Trp
1               5                   10                  15

<210> SEQ ID NO 18
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 18

Leu Phe Ser Val Pro Phe Asp Tyr Asn Leu Tyr Ser Asn Trp Trp
1               5                   10                  15
```

```
<210> SEQ ID NO 19
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 19

Met Ala Ser Ile Pro Tyr Asp Trp Asn Leu Tyr Gln Ser Trp Ala
1               5                   10                  15

<210> SEQ ID NO 20
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 20

Met Ala Ser Ile Pro Tyr Asp Trp Asn Leu Tyr Ser Ala Trp Ala
1               5                   10                  15

<210> SEQ ID NO 21
<211> LENGTH: 15
<212> TYPE: PRT
<213> ORGANISM: Unknown
<220> FEATURE:
<223> OTHER INFORMATION: Description of Unknown: Peptide
      sequence

<400> SEQUENCE: 21

Met Ala Ser Ile Pro Tyr Asp Trp His Leu Tyr Asn Ala Trp Ala
1               5                   10                  15

<210> SEQ ID NO 22
<211> LENGTH: 19
<212> TYPE: DNA
<213> ORGANISM: Aiptesia pulchella

<400> SEQUENCE: 22
gtrtcgacaa cgagtcrgg                                                  19

<210> SEQ ID NO 23
<211> LENGTH: 20
<212> TYPE: DNA
<213> ORGANISM: Anemonia viridansm

<400> SEQUENCE: 23
tgacatycca ccagttgctg                                                 20

<210> SEQ ID NO 24
<211> LENGTH: 15
<212> TYPE: PRT
<213> ORGANISM: Unknown
<220> FEATURE:
<223> OTHER INFORMATION: Description of Unknown: EqT-IV sequence

<400> SEQUENCE: 24

Leu Phe Ser Val Pro Tyr Asp Tyr Asn Trp Tyr Ser Asn Trp Trp
1               5                   10                  15

<210> SEQ ID NO 25
<211> LENGTH: 14
<212> TYPE: PRT
<213> ORGANISM: Unknown
```

```
<220> FEATURE:
<223> OTHER INFORMATION: Description of Unknown: Actinoporin Or-A
      sequence

<400> SEQUENCE: 25

Phe Ser Val Pro Tyr Asp Tyr Asn Leu Tyr Ser Asn Trp Trp
1               5                   10

<210> SEQ ID NO 26
<211> LENGTH: 15
<212> TYPE: PRT
<213> ORGANISM: Heteractis magnifica

<400> SEQUENCE: 26

Met Phe Ser Val Pro Phe Asp Tyr Asn Phe Tyr Ser Asn Trp Trp
1               5                   10                  15

<210> SEQ ID NO 27
<211> LENGTH: 15
<212> TYPE: PRT
<213> ORGANISM: Unknown
<220> FEATURE:
<223> OTHER INFORMATION: Description of Unknown: Avt-I RTX-A sequence

<400> SEQUENCE: 27

Met Phe Ser Val Pro Phe Asp Tyr Asn Leu Tyr Ser Asn Trp Trp
1               5                   10                  15

<210> SEQ ID NO 28
<211> LENGTH: 15
<212> TYPE: PRT
<213> ORGANISM: Unknown
<220> FEATURE:
<223> OTHER INFORMATION: Description of Unknown: Pstx20 sequence

<400> SEQUENCE: 28

Met Phe Ser Val Pro Phe Asp Tyr Asn Leu Tyr Thr Asn Trp Trp
1               5                   10                  15

<210> SEQ ID NO 29
<211> LENGTH: 15
<212> TYPE: PRT
<213> ORGANISM: Physcomitrella patens

<400> SEQUENCE: 29

Met Trp Ser Val Pro Phe Asp Tyr Asn Leu Tyr Ser Asn Trp Trp
1               5                   10                  15

<210> SEQ ID NO 30
<211> LENGTH: 15
<212> TYPE: PRT
<213> ORGANISM: Danio rerio

<400> SEQUENCE: 30

Met Phe Ser Val Pro Trp Asp Tyr Asn Leu Tyr Lys Asn Trp Phe
1               5                   10                  15

<210> SEQ ID NO 31
<211> LENGTH: 15
<212> TYPE: PRT
<213> ORGANISM: Tetraodon nigroviridis

<400> SEQUENCE: 31

Met Phe Ser Val Pro Phe Asp Tyr Asn Leu Tyr Lys Asn Trp Leu
1               5                   10                  15
```

```
<210> SEQ ID NO 32
<211> LENGTH: 17
<212> TYPE: PRT
<213> ORGANISM: Unknown
<220> FEATURE:
<223> OTHER INFORMATION: Description of Unknown: Peptide
      sequence

<400> SEQUENCE: 32

Cys Met Phe Ser Val Pro Phe Asp Tyr Asn Trp Tyr Ser Asn Trp Trp
1               5                   10                  15

Cys

<210> SEQ ID NO 33
<211> LENGTH: 213
<212> TYPE: PRT
<213> ORGANISM: Actinia equina

<400> SEQUENCE: 33

Met Ser Arg Leu Ile Ile Val Phe Ile Val Val Thr Met Ile Cys Ser
1               5                   10                  15

Ala Thr Ala Leu Pro Ser Lys Lys Ile Ile Asp Glu Asp Glu Glu Asp
            20                  25                  30

Glu Lys Arg Ser Ala Asp Val Ala Gly Ala Val Ile Asp Gly Ala Ser
        35                  40                  45

Leu Ser Phe Asp Ile Leu Lys Thr Val Leu Ala Leu Gly Asn Val Lys
    50                  55                  60

Arg Lys Ile Ala Val Gly Val Asp Asn Glu Ser Gly Lys Thr Trp Thr
65                  70                  75                  80

Ala Leu Asn Thr Tyr Phe Arg Ser Gly Thr Ser Asp Ile Val Leu Pro
                85                  90                  95

His Lys Val Pro His Gly Lys Ala Leu Leu Tyr Asn Gly Gln Lys Asp
            100                 105                 110

Arg Gly Pro Val Ala Thr Gly Ala Val Gly Val Leu Ala Tyr Leu Met
        115                 120                 125

Ser Asp Gly Asn Thr Leu Ala Val Leu Phe Ser Val Pro Tyr Asp Tyr
    130                 135                 140

Asn Trp Tyr Ser Asn Trp Trp Asn Val Arg Ile Tyr Lys Gly Lys Arg
145                 150                 155                 160

Arg Ala Asp Gln Arg Met Tyr Glu Glu Leu Tyr Tyr Asn Leu Ser Pro
                165                 170                 175

Phe Arg Gly Asp Asn Gly Trp His Thr Arg Asn Leu Gly Tyr Gly Leu
            180                 185                 190

Lys Ser Arg Gly Phe Met Asn Ser Gly His Ala Ile Leu Glu Ile
        195                 200                 205

His Val Ser Lys Ala
    210

<210> SEQ ID NO 34
<211> LENGTH: 175
<212> TYPE: PRT
<213> ORGANISM: Stichodactyla helianthus

<400> SEQUENCE: 34

Ala Leu Ala Gly Thr Ile Ile Ala Gly Ala Ser Leu Thr Phe Gln Val
1               5                   10                  15

Leu Asp Lys Val Leu Glu Glu Leu Gly Lys Val Ser Arg Lys Ile Ala
            20                  25                  30
```

```
Val Gly Ile Asp Asn Glu Ser Gly Thr Trp Thr Ala Leu Asn Ala
        35                  40                  45

Tyr Phe Arg Ser Gly Thr Thr Asp Val Ile Leu Pro Glu Phe Val Pro
 50                  55                  60

Asn Thr Lys Ala Leu Leu Tyr Ser Gly Arg Lys Asp Thr Gly Pro Val
 65                  70                  75                  80

Ala Thr Gly Ala Val Ala Phe Ala Tyr Tyr Met Ser Ser Gly Asn
                 85                  90                  95

Thr Leu Gly Val Met Phe Ser Val Pro Phe Asp Tyr Asn Trp Tyr Ser
                100                 105                 110

Asn Trp Trp Asp Val Lys Ile Tyr Ser Gly Lys Arg Ala Asp Gln
            115                 120                 125

Gly Met Tyr Glu Asp Leu Tyr Tyr Gly Asn Pro Tyr Arg Gly Asp Asn
            130                 135                 140

Gly Trp His Glu Lys Asn Leu Gly Tyr Gly Leu Arg Met Lys Gly Ile
145                 150                 155                 160

Met Thr Ser Ala Gly Glu Ala Lys Met Gln Ile Lys Ile Ser Arg
                165                 170                 175

<210> SEQ ID NO 35
<211> LENGTH: 176
<212> TYPE: PRT
<213> ORGANISM: Actinia equina

<400> SEQUENCE: 35

Asp Val Ala Gly Ala Val Ile Asp Gly Ala Ser Leu Ser Phe Asp Ile
 1               5                  10                  15

Leu Lys Thr Val Leu Glu Ala Leu Gly Asn Val Lys Arg Lys Ile Ala
                20                  25                  30

Val Gly Val Asp Asn Glu Ser Gly Lys Thr Trp Thr Ala Leu Asn Thr
            35                  40                  45

Tyr Phe Arg Ser Gly Thr Ser Asp Ile Val Leu Pro His Lys Val Pro
 50                  55                  60

His Gly Lys Ala Leu Leu Tyr Asn Gly Gln Lys Asp Arg Gly Pro Val
 65                  70                  75                  80

Ala Thr Gly Ala Val Gly Val Leu Ala Tyr Leu Met Ser Asp Gly Asn
                 85                  90                  95

Thr Leu Ala Val Leu Phe Ser Val Pro Tyr Asp Tyr Asn Trp Tyr Ser
                100                 105                 110

Asn Trp Trp Asn Val Arg Ile Tyr Lys Gly Lys Arg Arg Ala Asp Gln
            115                 120                 125

Arg Met Tyr Glu Glu Leu Tyr Tyr Asn Leu Ser Pro Phe Arg Gly Asp
            130                 135                 140

Asn Gly Trp His Thr Arg Asn Leu Gly Tyr Gly Leu Lys Ser Arg Gly
145                 150                 155                 160

Phe Met Asn Ser Ser Gly His Ala Ile Leu Glu Ile His Val Ser Lys
                165                 170                 175

<210> SEQ ID NO 36
<211> LENGTH: 114
<212> TYPE: PRT
<213> ORGANISM: Danio rerio

<400> SEQUENCE: 36

Met Thr Glu Ser Ala Glu Ala Val Ala Ala Asn Val Ser Ser Arg Arg
 1               5                  10                  15
```

```
His Ala Thr Val Glu Ile Thr Asn Leu Thr Asn Asn Tyr Cys Phe Leu
            20                  25                  30

Asn Pro Lys Val Tyr Leu Glu Asn Gly Glu Thr Ser Asn Pro Pro Gln
        35                  40                  45

Pro Thr Val Arg Pro Leu Lys Thr Glu Val Cys Thr Phe Ser Lys Ser
    50                  55                  60

Ala Ala His Ala Thr Gly Ala Asn Gly Ser Gly Ile Asn Phe Glu Gly
65                  70                  75                  80

Lys Asn Leu Asp Ile Arg Ala Thr Met Cys Pro Met Gly Arg Ala Ile
                85                  90                  95

Val Lys Val Glu Val Trp Asp Lys Leu Leu Ser Pro Met Ala Gln Met
            100                 105                 110

Asp Cys

<210> SEQ ID NO 37
<211> LENGTH: 156
<212> TYPE: PRT
<213> ORGANISM: Actinia equina

<400> SEQUENCE: 37

Leu Glu Ala Leu Gly Asn Val Lys Arg Lys Ile Ala Val Gly Val Asp
1               5                   10                  15

Asn Glu Ser Gly Lys Thr Trp Thr Ala Leu Asn Thr Tyr Phe Arg Ser
            20                  25                  30

Gly Thr Ser Asp Ile Val Leu Pro His Lys Val Pro His Gly Lys Ala
        35                  40                  45

Leu Leu Tyr Asn Gly Gln Lys Asp Arg Gly Pro Val Ala Thr Gly Ala
    50                  55                  60

Val Gly Val Leu Ala Tyr Leu Met Ser Asp Gly Asn Thr Leu Ala Val
65                  70                  75                  80

Leu Phe Ser Val Pro Tyr Asp Tyr Asn Trp Tyr Ser Asn Trp Trp Asn
                85                  90                  95

Val Arg Ile Tyr Lys Gly Lys Arg Arg Ala Asp Gln Arg Met Tyr Glu
            100                 105                 110

Glu Leu Tyr Tyr Asn Leu Ser Pro Phe Arg Gly Asp Asn Gly Trp His
        115                 120                 125

Thr Arg Asn Leu Gly Tyr Gly Leu Lys Ser Arg Gly Phe Met Asn Ser
    130                 135                 140

Ser Gly His Ala Ile Leu Glu Ile His Val Ser Lys
145                 150                 155

<210> SEQ ID NO 38
<211> LENGTH: 166
<212> TYPE: PRT
<213> ORGANISM: Danio rerio

<400> SEQUENCE: 38

Val Ala Ala Asn Val Ser Ser Arg Arg His Ala Thr Val Glu Ile Thr
1               5                   10                  15

Asn Leu Thr Asn Asn Tyr Cys Phe Leu Asn Pro Lys Val Tyr Leu Glu
            20                  25                  30

Asn Gly Glu Thr Ser Asn Pro Pro Gln Pro Thr Val Arg Pro Leu Lys
        35                  40                  45

Thr Glu Val Cys Thr Phe Ser Lys Ser Ala Ala His Ala Thr Gly Ser
    50                  55                  60
```

```
Val Gly Val Leu Thr Tyr Asp Leu Phe Glu Arg Arg Asn Asp Tyr
 65                  70                  75                  80

Thr Glu Thr Leu Ala Ile Met Phe Ser Val Pro Trp Asp Tyr Asn Leu
                 85                  90                  95

Tyr Lys Asn Trp Phe Ala Val Gly Ile Tyr Pro Lys Gly Lys Glu Cys
            100                 105                 110

Asp Gln Ala Leu Tyr Lys Glu Met Tyr Tyr Gln Lys Asn Gln His Gly
            115                 120                 125

Phe Val Arg Glu Glu Ala Asn Gly Ser Gly Ile Asn Phe Glu Gly Lys
        130                 135                 140

Asn Leu Asp Ile Arg Ala Thr Met Cys Pro Met Gly Arg Ala Ile Val
145                 150                 155                 160

Lys Val Glu Val Trp Asp
                165

<210> SEQ ID NO 39
<211> LENGTH: 181
<212> TYPE: PRT
<213> ORGANISM: Tetraodon nigroviridis

<400> SEQUENCE: 39

Met Glu Ser Ala Glu Ala Val Ala Ala Asp Val Ser Arg Ser Arg Ser
1               5                   10                  15

Val Thr Ile Glu Ile Ser Asn Leu Thr Lys Asn Tyr Cys Leu Ile Asn
            20                  25                  30

Pro Arg Val Tyr Leu Glu Ser Gly Glu Thr Tyr Asn Pro Pro Gln Pro
        35                  40                  45

Thr Val Arg Pro Leu Met Thr Glu Val Cys Thr Phe Ser Lys Ser Ser
    50                  55                  60

Gly Ile Pro Thr Gly Ser Val Gly Val Leu Thr Tyr Glu Leu Leu Glu
65                  70                  75                  80

Arg Arg Ser Thr Met Leu Pro Glu Thr Leu Ala Ile Met Phe Ser Val
                85                  90                  95

Pro Tyr Asp Tyr Ser Phe Tyr Asn Asn Trp Phe Ala Val Gly Ile Tyr
            100                 105                 110

Glu Thr Gly Thr Lys Cys Asn Glu Gly Leu Tyr Lys Gln Met Tyr Asn
            115                 120                 125

Glu Lys Lys Gln Ala Glu His Gly Phe Val Arg Glu Lys Ala Asn Gly
        130                 135                 140

Ser Gly Ile Asn Tyr Val Gly Gly Asn Leu Asp Ile Arg Ala Thr Met
145                 150                 155                 160

Asn Pro Leu Gly Lys Ala Ile Met Lys Val Glu Val Trp Asp Ala Phe
                165                 170                 175

Phe Pro Phe Ser Glu
            180

<210> SEQ ID NO 40
<211> LENGTH: 157
<212> TYPE: PRT
<213> ORGANISM: Actinia equina

<400> SEQUENCE: 40

Leu Glu Ala Leu Gly Asn Val Lys Arg Lys Ile Ala Val Gly Val Asp
1               5                   10                  15

Asn Glu Ser Gly Lys Thr Trp Thr Ala Leu Asn Thr Tyr Phe Arg Ser
            20                  25                  30
```

```
Gly Thr Ser Asp Ile Val Leu Pro His Lys Val Pro His Gly Lys Ala
            35                  40                  45

Leu Leu Tyr Asn Gly Gln Lys Asp Arg Gly Pro Val Ala Thr Gly Ala
 50                  55                  60

Val Gly Val Leu Ala Tyr Leu Met Ser Asp Gly Asn Thr Leu Ala Val
 65                  70                  75                  80

Leu Phe Ser Val Pro Tyr Asp Tyr Asn Trp Tyr Ser Asn Trp Trp Asn
                 85                  90                  95

Val Arg Ile Tyr Lys Gly Lys Arg Arg Ala Asp Gln Arg Met Tyr Glu
            100                 105                 110

Glu Leu Tyr Tyr Asn Leu Ser Pro Phe Arg Gly Asp Asn Gly Trp His
            115                 120                 125

Thr Arg Asn Leu Gly Tyr Gly Leu Lys Ser Arg Gly Phe Met Asn Ser
130                 135                 140

Ser Gly His Ala Ile Leu Glu Ile His Val Ser Lys Ala
145                 150                 155
```

```
<210> SEQ ID NO 41
<211> LENGTH: 169
<212> TYPE: PRT
<213> ORGANISM: Tetraodon nigroviridis

<400> SEQUENCE: 41

Val Ala Ala Asp Val Ser Arg Ser Arg Ser Val Thr Ile Glu Ile Ser
 1               5                  10                  15

Asn Leu Thr Lys Asn Tyr Cys Leu Ile Asn Pro Arg Val Tyr Leu Glu
            20                  25                  30

Ser Gly Glu Thr Tyr Asn Pro Pro Gln Pro Thr Val Arg Pro Leu Met
            35                  40                  45

Thr Glu Val Cys Thr Phe Ser Lys Ser Ser Gly Ile Pro Thr Gly Ser
 50                  55                  60

Val Gly Val Leu Thr Tyr Glu Leu Leu Glu Arg Arg Ser Thr Met Leu
 65                  70                  75                  80

Pro Glu Thr Leu Ala Ile Met Phe Ser Val Pro Tyr Asp Tyr Ser Phe
                 85                  90                  95

Tyr Asn Asn Trp Phe Ala Val Gly Ile Tyr Glu Thr Gly Thr Lys Cys
            100                 105                 110

Asn Glu Gly Leu Tyr Lys Gln Met Tyr Asn Glu Lys Lys Gln Ala Glu
            115                 120                 125

His Gly Phe Val Arg Glu Lys Ala Asn Gly Ser Gly Ile Asn Tyr Val
130                 135                 140

Gly Gly Asn Leu Asp Ile Arg Ala Thr Met Asn Pro Leu Gly Lys Ala
145                 150                 155                 160

Ile Met Lys Val Glu Val Trp Asp Ala
                 165
```

```
<210> SEQ ID NO 42
<211> LENGTH: 199
<212> TYPE: PRT
<213> ORGANISM: Physcomitrella patens

<400> SEQUENCE: 42

Met Val Val His Leu Ile Ala Met Gly Leu Arg Tyr Ser Glu Thr Ile
 1               5                  10                  15

Met Lys Thr Ala Arg Met Ala Glu Ala Ile Ile Pro Ala Ala Glu Leu
            20                  25                  30
```

```
Ser Ile Lys Thr Leu Gln Asn Ile Val Glu Gly Ile Thr Gly Val Asp
         35                  40                  45

Arg Lys Ile Ala Ile Gly Phe Lys Asn Leu Thr Asp Tyr Thr Leu Glu
 50                  55                  60

Asn Leu Gly Val Tyr Phe Asn Ser Gly Ser Ser Asp Arg Ser Ile Ala
 65                  70                  75                  80

Tyr Lys Ile Asn Ala Gln Glu Ala Leu Leu Phe Ser Ala Arg Lys Ser
                 85                  90                  95

Asp His Thr Ala Arg Gly Thr Val Gly Thr Phe Ser Tyr Tyr Ile Gln
            100                 105                 110

Asp Glu Asp Lys Thr Val His Val Met Trp Ser Val Pro Phe Asp Tyr
            115                 120                 125

Asn Leu Tyr Ser Asn Trp Trp Asn Ile Ala Val Val Asp Gly Arg Gln
130                 135                 140

Pro Pro Asp Ser Asn Val His Asp Asn Leu Tyr Asn Gly Ser Gly Gly
145                 150                 155                 160

Met Pro Tyr Pro Asn Lys Pro Asp Gln Tyr Ile Asn Asn Glu Gln Lys
                165                 170                 175

Gly Phe His Leu Phe Gly Ser Met Thr Asn Asn Gly Gln Ala Thr Ile
            180                 185                 190

Glu Val Glu Leu Lys Lys Ala
            195

<210> SEQ ID NO 43
<211> LENGTH: 180
<212> TYPE: PRT
<213> ORGANISM: Actinia equina

<400> SEQUENCE: 43

Arg Ser Ala Asp Val Ala Gly Ala Val Ile Asp Gly Ala Ser Leu Ser
 1               5                  10                  15

Phe Asp Ile Leu Lys Thr Val Leu Glu Ala Leu Gly Asn Val Lys Arg
                20                  25                  30

Lys Ile Ala Val Gly Val Asp Asn Glu Ser Gly Lys Thr Trp Thr Ala
            35                  40                  45

Leu Asn Thr Tyr Phe Arg Ser Gly Thr Ser Asp Ile Val Leu Pro His
 50                  55                  60

Lys Val Pro His Gly Lys Ala Leu Leu Tyr Asn Gly Gln Lys Asp Arg
 65                  70                  75                  80

Gly Pro Val Ala Thr Gly Ala Val Gly Val Leu Ala Tyr Leu Met Ser
                 85                  90                  95

Asp Gly Asn Thr Leu Ala Val Leu Phe Ser Val Pro Tyr Asp Tyr Asn
            100                 105                 110

Trp Tyr Ser Asn Trp Trp Asn Val Arg Ile Tyr Lys Gly Lys Arg Arg
            115                 120                 125

Ala Asp Gln Arg Met Tyr Glu Glu Leu Tyr Tyr Asn Leu Ser Pro Phe
130                 135                 140

Arg Gly Asp Asn Gly Trp His Thr Arg Asn Leu Gly Tyr Gly Leu Lys
145                 150                 155                 160

Ser Arg Gly Phe Met Asn Ser Ser Gly His Ala Ile Leu Glu Ile His
                165                 170                 175

Val Ser Lys Ala
            180

<210> SEQ ID NO 44
```

<211> LENGTH: 182
<212> TYPE: PRT
<213> ORGANISM: Physcomitrella patens

<400> SEQUENCE: 44

```
Lys Thr Ala Arg Met Ala Glu Ala Ile Ile Pro Ala Ala Glu Leu Ser
1               5                   10                  15

Ile Lys Thr Leu Gln Asn Ile Val Glu Gly Ile Thr Gly Val Asp Arg
            20                  25                  30

Lys Ile Ala Ile Gly Phe Lys Asn Leu Thr Asp Tyr Thr Leu Glu Asn
        35                  40                  45

Leu Gly Val Tyr Phe Asn Ser Gly Ser Ser Asp Arg Ser Ile Ala Tyr
    50                  55                  60

Lys Ile Asn Ala Gln Glu Ala Leu Leu Phe Ser Ala Arg Lys Ser Asp
65                  70                  75                  80

His Thr Ala Arg Gly Thr Val Gly Thr Phe Ser Tyr Tyr Ile Gln Asp
                85                  90                  95

Glu Asp Lys Thr Val His Val Met Trp Ser Val Pro Phe Asp Tyr Asn
            100                 105                 110

Leu Tyr Ser Asn Trp Trp Asn Ile Ala Val Val Asp Gly Arg Gln Pro
        115                 120                 125

Pro Asp Ser Asn Val His Asp Asn Leu Tyr Asn Gly Ser Gly Gly Met
    130                 135                 140

Pro Tyr Pro Asn Lys Pro Asp Gln Tyr Ile Asn Asn Glu Gln Lys Gly
145                 150                 155                 160

Phe His Leu Phe Gly Ser Met Thr Asn Asn Gly Gln Ala Thr Ile Glu
                165                 170                 175

Val Glu Leu Lys Lys Ala
            180
```

<210> SEQ ID NO 45
<211> LENGTH: 204
<212> TYPE: PRT
<213> ORGANISM: Gallus gallus

<400> SEQUENCE: 45

```
Met Pro Pro Lys Glu Lys Lys Glu Asn Asp Lys Pro Cys Asn Asp Asn
1               5                   10                  15

Cys Gln Pro Lys Pro Gln Gly Lys Gly Val Glu Ser Leu Met Lys Asn
            20                  25                  30

Ile Asp Val Cys Arg Ser Val Gly Leu Glu Ile Ile Asn Arg Thr Arg
        35                  40                  45

Thr Val Thr Leu Thr Asp Phe Arg Ser Tyr Cys Phe Ser Gly Lys Ile
    50                  55                  60

Val Thr Thr Leu Pro Phe Glu Ile Gly Pro Asp Ser Lys Gly Ile Cys
65                  70                  75                  80

Ile Phe Ala Lys Thr Pro Tyr Ser Leu Arg Gly Ser Val Gly Thr Val
                85                  90                  95

Val Cys Lys Ala Asp Thr Phe Phe Leu Ala Ile Thr Phe Ser Asn Pro
            100                 105                 110

Tyr Asp Tyr Ile Leu Tyr Lys Ile Glu Phe Ala Leu Glu Ile Phe Thr
        115                 120                 125

Glu Pro Asn His Leu Gly Asn Leu Gly Asp Val Phe Ser Lys Met Met
    130                 135                 140

Lys Ser Lys Pro Tyr Cys Gly Ser Ser Leu Phe Gln Arg Ala Val Leu
145                 150                 155                 160
```

```
Glu Ser Glu His Glu Thr Leu Glu Val Ser Lys Gly Ser Ile Arg Val
                165                 170                 175

Gln Ala Lys Met Ser Asn Asn Arg Lys Ala Ile Leu Lys Val Gln Val
            180                 185                 190

Glu Asp Met Asp Pro Pro Tyr Ser Lys Gly Met
        195                 200

<210> SEQ ID NO 46
<211> LENGTH: 166
<212> TYPE: PRT
<213> ORGANISM: Gallus gallus

<400> SEQUENCE: 46

Leu Met Lys Asn Ile Asp Val Cys Arg Ser Val Gly Leu Glu Ile Ile
1               5                   10                  15

Asn Arg Thr Arg Thr Val Thr Leu Thr Asp Phe Arg Ser Tyr Cys Phe
            20                  25                  30

Ser Gly Lys Ile Val Thr Thr Leu Pro Phe Glu Ile Gly Pro Asp Ser
        35                  40                  45

Lys Gly Ile Cys Ile Phe Ala Lys Thr Pro Tyr Ser Leu Arg Gly Ser
    50                  55                  60

Val Gly Thr Val Val Cys Lys Ala Asp Thr Phe Phe Leu Ala Ile Thr
65                  70                  75                  80

Phe Ser Asn Pro Tyr Asp Tyr Ile Leu Tyr Lys Ile Glu Phe Ala Leu
                85                  90                  95

Glu Ile Phe Thr Glu Pro Asn His Leu Gly Asn Leu Gly Asp Val Phe
            100                 105                 110

Ser Lys Met Met Lys Ser Lys Pro Tyr Cys Gly Ser Ser Leu Phe Gln
        115                 120                 125

Arg Ala Val Leu Glu Ser Glu His Glu Thr Leu Glu Val Ser Lys Gly
    130                 135                 140

Ser Ile Arg Val Gln Ala Lys Met Ser Asn Asn Arg Lys Ala Ile Leu
145                 150                 155                 160

Lys Val Gln Val Glu Asp
                165

<210> SEQ ID NO 47
<211> LENGTH: 220
<212> TYPE: PRT
<213> ORGANISM: Ornithorhynchus anatinus

<400> SEQUENCE: 47

Met Ala Gln Thr Ile Glu His Leu Val His Glu Val Glu Ala Gly Arg
1               5                   10                  15

Cys Val Gly Ile Glu Ile Thr Asn Thr Thr Asn Met Thr Phe Arg Ser
            20                  25                  30

Pro Arg Thr Phe Cys Phe Ser Gly His Thr Leu Thr Pro Pro Thr Pro
        35                  40                  45

Ile Ile His Pro Asn Asn Ala Gly Phe Cys Ile Phe Val Lys Arg Lys
    50                  55                  60

Phe Ser Leu Arg Gly Ser Val Gly Leu Leu Val Tyr Glu Ile Glu Asp
65                  70                  75                  80

Gln Thr Leu Ala Ile Met Phe Ser Asn Pro Phe Asp Tyr Asn Phe Phe
                85                  90                  95

Lys Val Glu Phe Ala Val Ala Leu Ser Gly Tyr Lys Glu Glu Thr Gln
            100                 105                 110
```

```
Asp Leu Lys Ala Phe Phe Glu Leu Leu Tyr His Glu Lys Gln Lys Gly
            115                 120                 125

Trp Leu Lys Met Ala Lys Glu Lys Leu Cys Glu Cys Gln Cys Pro Val
    130                 135                 140

Ser Leu Glu Asn Asn Gly Ile Arg Val Thr Ala Thr Met Ser Asn Asn
145                 150                 155                 160

Ala Lys Ala Ile Ile Lys Leu Ser Ser Pro Asp Ala Lys Pro Pro Glu
                165                 170                 175

Gly Asp Val Ala Asp Val Gln Pro Thr Thr Val Arg Arg Pro Asn Pro
                180                 185                 190

Pro Pro Phe Pro Ser Pro Arg Pro Arg Ile Gly Ser Asp Leu Thr Gly
                195                 200                 205

Asp Gln Leu Ala Thr Leu Asp Phe Glu Ser Gly Lys
            210                 215                 220

<210> SEQ ID NO 48
<211> LENGTH: 157
<212> TYPE: PRT
<213> ORGANISM: Actinia equina

<400> SEQUENCE: 48

Leu Glu Ala Leu Gly Asn Val Lys Arg Lys Ile Ala Val Gly Val Asp
1               5                   10                  15

Asn Glu Ser Gly Lys Thr Trp Thr Ala Leu Asn Thr Tyr Phe Arg Ser
            20                  25                  30

Gly Thr Ser Asp Ile Val Leu Pro His Lys Val Pro His Gly Lys Ala
        35                  40                  45

Leu Leu Tyr Asn Gly Gln Lys Asp Arg Gly Pro Val Ala Thr Gly Ala
    50                  55                  60

Val Gly Val Leu Ala Tyr Leu Met Ser Asp Gly Asn Thr Leu Ala Val
65                  70                  75                  80

Leu Phe Ser Val Pro Tyr Asp Tyr Asn Trp Tyr Ser Asn Trp Trp Asn
                85                  90                  95

Val Arg Ile Tyr Lys Gly Lys Arg Arg Ala Asp Gln Arg Met Tyr Glu
            100                 105                 110

Glu Leu Tyr Tyr Asn Leu Ser Pro Phe Arg Gly Asp Asn Gly Trp His
        115                 120                 125

Thr Arg Asn Leu Gly Tyr Gly Leu Lys Ser Arg Gly Phe Met Asn Ser
    130                 135                 140

Ser Gly His Ala Ile Leu Glu Ile His Val Ser Lys Ala
145                 150                 155

<210> SEQ ID NO 49
<211> LENGTH: 165
<212> TYPE: PRT
<213> ORGANISM: Ornithorhynchus anatinus

<400> SEQUENCE: 49

Leu Val His Glu Val Glu Ala Gly Arg Cys Val Gly Ile Glu Ile Thr
1               5                   10                  15

Asn Thr Thr Asn Met Thr Phe Arg Ser Pro Arg Thr Phe Cys Phe Ser
            20                  25                  30

Gly His Thr Leu Thr Pro Pro Thr Pro Ile Ile His Pro Asn Asn Ala
        35                  40                  45

Gly Phe Cys Ile Phe Val Lys Arg Lys Phe Ser Leu Arg Gly Ser Val
    50                  55                  60
```

```
Gly Leu Leu Val Tyr Glu Ile Glu Asp Gln Thr Leu Ala Ile Met Phe
 65                  70                  75                  80

Ser Asn Pro Phe Asp Tyr Asn Phe Phe Lys Val Glu Phe Ala Val Ala
                 85                  90                  95

Leu Ser Gly Tyr Lys Glu Glu Thr Gln Asp Leu Lys Ala Phe Phe Glu
            100                 105                 110

Leu Leu Tyr His Glu Lys Gln Lys Gly Trp Leu Lys Met Ala Lys Glu
            115                 120                 125

Lys Leu Cys Glu Cys Gln Cys Pro Val Ser Leu Glu Asn Asn Gly Ile
130                 135                 140

Arg Val Thr Ala Thr Met Ser Asn Asn Ala Lys Ala Ile Ile Lys Leu
145                 150                 155                 160

Ser Ser Pro Asp Ala
            165

<210> SEQ ID NO 50
<211> LENGTH: 265
<212> TYPE: DNA
<213> ORGANISM: Aiptasia pulchella

<400> SEQUENCE: 50
gtgtcgccaa cgagtcggga tgcacttggg aaaagccaaa tacatacttc ttctctggta      60
ctgaggtata aagtgcctcc ctctaaagct tgagaataaa aaagcacttt tgtacggccc     120
acgtaagaca cagggcctg ttgccacggg agctgttgga gtgctcactt acaaaatgtt     180
gtgcaccaat gagacgaaca ctctggctgt tcttttcagt gtacccttcg actacaactt     240
gtacagcaac tggtggaaat gtcaa                                           265

<210> SEQ ID NO 51
<211> LENGTH: 14
<212> TYPE: PRT
<213> ORGANISM: Aiptasia pulchella

<400> SEQUENCE: 51

Phe Ser Val Pro Phe Asp Tyr Asn Leu Tyr Ser Asn Trp Trp
 1               5                  10

<210> SEQ ID NO 52
<211> LENGTH: 254
<212> TYPE: DNA
<213> ORGANISM: Anemonia viridans
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (70)..(70)
<223> OTHER INFORMATION: a, c, t, g, unknown or other

<400> SEQUENCE: 52
tgtgtcgaca acgagtcggg caagacgtgg accgcantga acacatactt ccgttctggc      60
acctctgatn tcrtccttcc ccatacagtt ccacatggta aggcactgct ctacaacggt     120
cagaaagatc gtggtccagt tgcgactggc gtggttggag tacttgctta tgccatgagc     180
gatggaaaca ccctggccgt tttgttcagc rttccctatg actataacct gtacagcaac     240
tggtggaatg tcaa                                                       254

<210> SEQ ID NO 53
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Arg Gln Arg Val Gly Met His Leu Gly Lys Ala Lys Tyr Ile Leu
1               5                   10                  15

Leu Leu Trp Tyr
            20

<210> SEQ ID NO 54
<211> LENGTH: 15
<212> TYPE: PRT
<213> ORGANISM: Artificial Sequence
<220> FEATURE:
<221> NAME/KEY: source
<223> OTHER INFORMATION: Description of Artificial Sequence: Synthetic
      peptide

<400> SEQUENCE: 54

Met Phe Ser Val Pro Phe Asp Tyr Asn Trp Tyr Ser Asn Trp Trp
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Phe Ser Val Pro Phe Asp Tyr Asn Trp Tyr Ser Asn Trp Trp Cys
1               5                   10                  15

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Phe Asp Tyr Asn Trp Tyr Cys
1               5

<210> SEQ ID NO 57
<211> LENGTH: 15
<212> TYPE: PRT
<213> ORGANISM: Unknown
<220> FEATURE:
<223> OTHER INFORMATION: Description of Unknown: Peptide sequence

<400> SEQUENCE: 57

Leu Phe Ser Val Pro Tyr Asp Tyr Asn Leu Tyr Ser Asn Trp Trp
1               5                   10                  15

<210> SEQ ID NO 58
<211> LENGTH: 15
<212> TYPE: PRT
<213> ORGANISM: Unknown
<220> FEATURE:
<223> OTHER INFORMATION: Description of Unknown: Peptide sequence
```

```
<400> SEQUENCE: 58

Met Phe Ser Val Pro Tyr Asp Tyr Asn Leu Tyr Ser Asn Trp Val
1               5                   10                  15

<210> SEQ ID NO 59
<211> LENGTH: 15
<212> TYPE: PRT
<213> ORGANISM: Unknown
<220> FEATURE:
<223> OTHER INFORMATION: Description of Unknown: Peptide sequence

<400> SEQUENCE: 59

Leu Phe Ser Val Pro Phe Asp Tyr Asn Phe Tyr Ser Asn Trp Trp
1               5                   10                  15

<210> SEQ ID NO 60
<211> LENGTH: 15
<212> TYPE: PRT
<213> ORGANISM: Unknown
<220> FEATURE:
<223> OTHER INFORMATION: Description of Unknown: Peptide sequence

<400> SEQUENCE: 60

Leu Phe Ser Ile Pro Phe Asp Tyr Asn Leu Tyr Ser Asn Trp Trp
1               5                   10                  15

<210> SEQ ID NO 61
<211> LENGTH: 15
<212> TYPE: PRT
<213> ORGANISM: Unknown
<220> FEATURE:
<223> OTHER INFORMATION: Description of Unknown: Peptide sequence

<400> SEQUENCE: 61

Met Phe Ser Val Pro Phe Asp Tyr Asn Leu Tyr Lys Asn Trp Phe
1               5                   10                  15

<210> SEQ ID NO 62
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Ile Lys Cys Leu Pro Leu Lys Leu Glu Asn Lys Lys Ala Leu Leu
1               5                   10                  15

Tyr Gly Pro Arg Lys Thr Thr Gly Pro Val Ala Thr Gly Ala Val Gly
                20                  25                  30

Val Leu Thr Tyr Lys Met Leu Cys Thr Asn Glu Thr Asn Thr Leu Ala
            35                  40                  45

Val Leu Phe Ser Val Pro Phe Asp Tyr Asn Leu Tyr Ser Asn Trp Trp
        50                  55                  60

Lys Cys Gln
65
```

PEPTIDES AND COMPOSITIONS FOR PREVENTION OF CELL ADHESION AND METHODS OF USING SAME

CROSS-REFERENCE TO RELATED PATENT APPLICATIONS

This application is a continuation of U.S. patent application Ser. No. 13/120,049, which in turn is a U.S. National Stage of PCT/IB2009/006926, filed Sep. 23, 2009, and claims priority of U.S. Provisional Patent Application No. 61/136,673, filed Sep. 24, 2008. The disclosures of the prior applications are incorporated by reference herein in their entirety.

SEQUENCE LISTING

The instant application contains a Sequence Listing which has been submitted in ASCII format via EFS-WEB and is hereby incorporated by reference in its entirety. Said ASCII copy, created on Dec. 8, 2014, is named 095432-0125_SL.txt and is 38,421 bytes in size.

FIELD OF THE INVENTION

The present invention relates to isolated natural peptides and their use in prevention of cell adhesion.

BACKGROUND OF THE INVENTION

Microorganisms can live and proliferate as individual cells swimming freely in the environment (as plankton), or they can grow as highly organized, multicellular communities encased in a self-produced polymeric matrix in close association with surfaces and interfaces. The latter microbial lifestyle is referred to as biofilms. Biofilm formation represents an ancient, protected mode of growth that allows microbial survival in hostile environments and allows microorganisms to disperse and colonize new niches [Hall-Stoodley et al., Nat Rev Microbiol. (2004) 2(2):95-108].

The composition of biofilms is complex and variable among different microbial species and even within the same species under different environmental conditions. Nonetheless, biofilm formation represents the normal lifestyle of microorganism in the environment and all microbes can make biofilms. Previous studies revealed that bacterial biofilm formation progresses through multiple developmental stages differing in protein profiles [Sauer et al., J Bacteriol. (2002) 184(4):1140-54], beginning with attachment to surface, followed by the immigration and division to form microcolonies and finally maturation involving expression of matrix polymers. Bacteria within each biofilm stage display phenotypes and possess properties that are markedly different from those of the same group growing planktonically [Sauer et al., J Bacteriol. (2004) 186(21):7312-26].

Biofilms are a major cause of systemic infections (e.g. nosocomial infections) in humans. In the body, biofilms can be associated with tissues (e.g., inner ears, teeth, gums, lungs, heart valves and the urogenital tract). An estimated 65% of bacterial infections in humans are biofilm in nature. Additionally, after forming biofilms, microorganisms tend to change their characteristics, sometimes drastically, such that doses of antibiotics which normally kill the organisms in suspended cultures are completely ineffective against the same microorganisms when the organisms are in attached or conglomerate biofilm form (U.S. Pat. No. 7,189,351).

One of the principal concerns with respect to products that are introduced into the body (e.g., contact lenses, central venous catheters, mechanical heart valves and pacemakers) or provide a pathway into the body is microbial infection and invariably biofilm formation. As these infections are difficult to treat with antibiotics, removal of the device is often necessitated, which is traumatic to the patient and increases the medical cost. Accordingly, for such medical apparatuses, the art has long sought means and methods of rendering those medical apparatuses and devices antimicrobial.

PCT Application No. WO 06/006172 discloses the use of anti-amyloid agents, such as aromatic compounds, for inhibiting formation or disintegrating a pre existing biofilm. The application discloses that compounds preventing amyloid fibril formation in Alzheimer can act against fibril formation in biofilms, and concludes that amino acids having an aromatic arm are effective against biofilms. However, the analysis was limited to full length sequences.

SUMMARY OF THE INVENTION

The present invention provides broad spectrum natural factors that interfere with biofilm formation at its initial stages, in a wide range of microorganisms. From these natural factors, peptides with high conservation sequences were isolated, and showed high activity in prevention of microbial adherence in its synthetic conformation. The conserved sequence is found in several marine organisms, including various known species of sea anemone, several fish (including *Danio rerio*—zebra fish), and in moss *Physcomitrella patens* subsp. *Patens*.

All factors mentioned above show activity that is exclusively directed to the prevention of bacterial substrate adhesion and the derived biofilm formation. It is devoid of the commonly observed lethal bactericidal activity, revealed by the antibiotic peptides and secondary metabolites, which provides a strong selective pressure for rapid natural selection by the intensive microbial "biotic potential." On the other hand a wide range inhibition of bacterial colonization antagonizes a fundamental mechanism of bacterial survival. Therefore an adaptive modification of such mechanism has a low likelihood due to its vitality.

Sher et al. (Toxicon 45: 865-879, 2005) identified putative biologically active proteins and polypeptides expressed by hydrae which could be components of its allomonal system, using a bioinformatics approach. Hydrae were shown to express orthologs of cnidarian phospholipase A2 toxins and cytolysicns belonging to the actinoporin family, and to express proteins similar to elapid-like phospholipases, cysteine-rich secretory proteins (CRISP), prokineticin-like polypeptides and toxic deoxyribonucleases.

The specific sequences responsible for cytotoxic activity in peptides isolated from natural sources have not hitherto been identified.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method. The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

As used herein the term "about" refers to ±10%.

Other features and advantages of the invention will be apparent from the following detailed description, and from the claims.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 shows the crystal structure of the 1GWY chain A of the water-soluble state of the pore-forming cytolysin sticholysin Ii, the active region marked in yellow; (and circled)

FIG. 2 shows the crystal structure of the 1GWY chain B of the water-soluble state of the pore-forming cytolysin sticholysin Ii, the active region marked in yellow; (and circled)

FIG. 3 shows the structure of the IKD6 chain A of the eukaryotic pore-forming cytolysin equinatoxin Ii, the active region marked in yellow; (and circled)

FIG. 4 shows the 3-dimensional construct of an equinatoxin mutant, the active region marked in yellow; (and circled)

DESCRIPTION OF THE PREFERRED EMBODIMENTS

Figure 5:
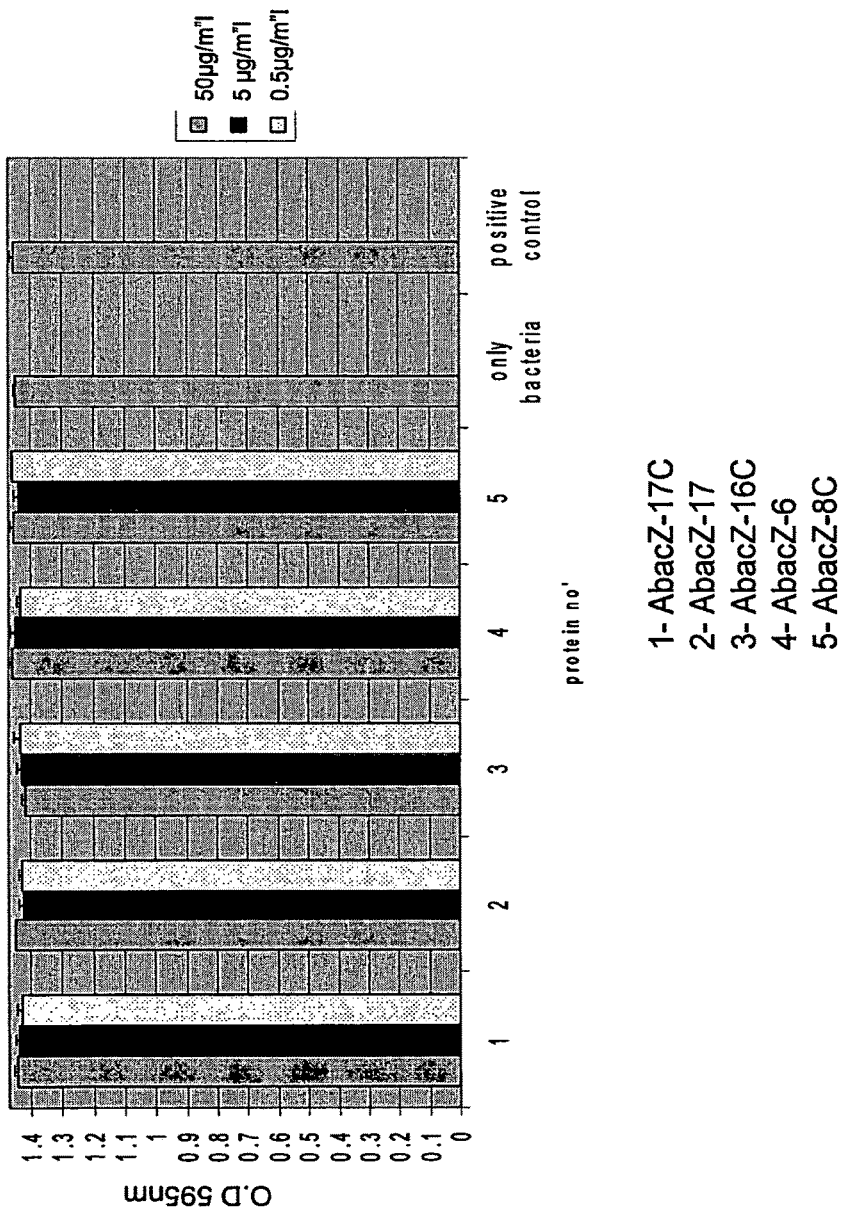
FIG. 5 is a bar chart showing the effects of different concentrations of synthetic proteins on growth of *Pseudomonas aeruginosa* ATee 27853 over 24 hours; No bactericidal or bacteriostatic effect.
Figure 6:
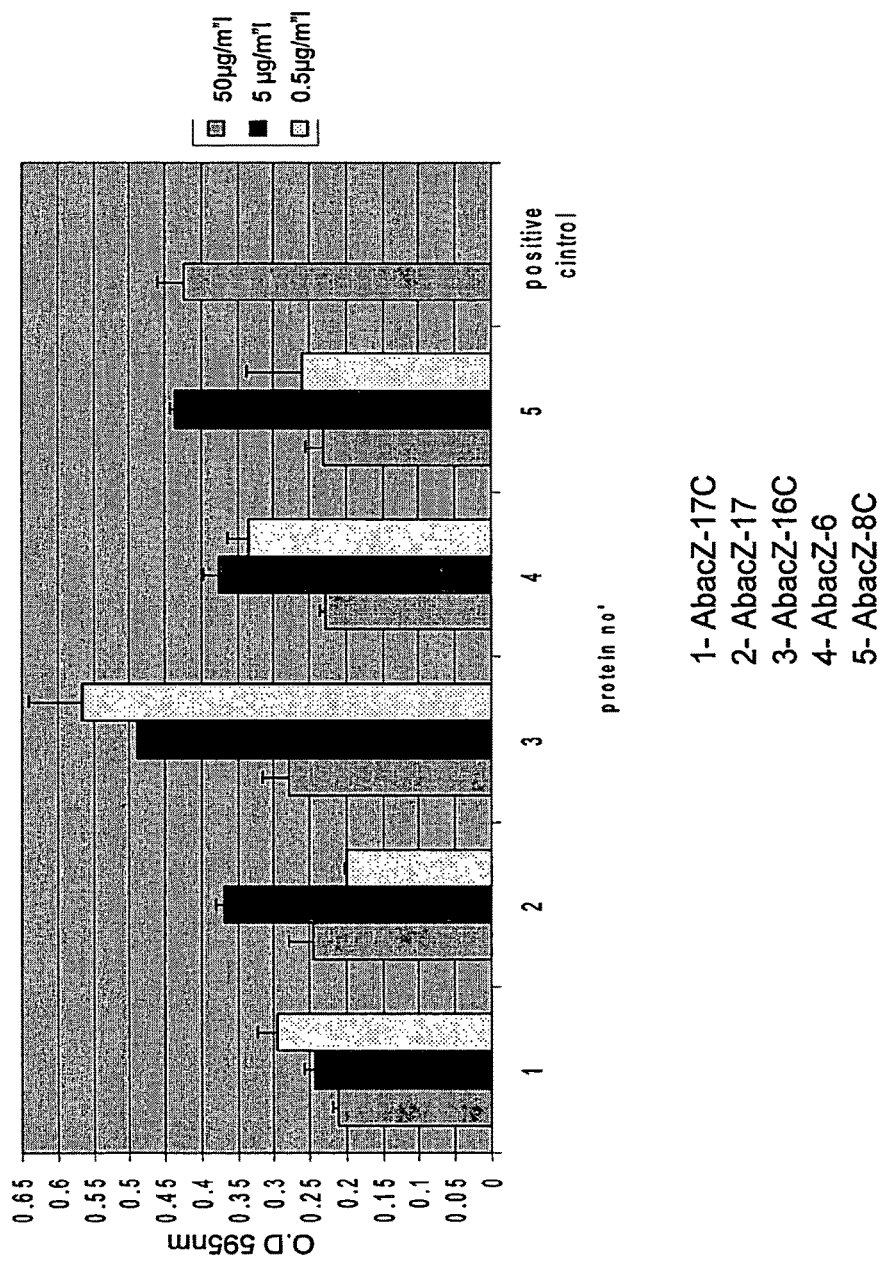
FIG. 6 is a bar chart showing the effects of different concentrations of synthetic proteins on biofilm formation by *Pseudomonas aeruginosa* ATee 27853 over 24 hours.

The present invention is of compositions comprising an isolated peptide which has one or more effects relating to prevention of bacterial substrate adhesion and the derived biofilm formation, and optionally also prevention of cell-cell adhesion. Other effects may also optionally be provided, additionally or alternatively. As a non-limiting example, the peptide may optionally and preferably comprise a sequence selected from the group consisting of YDYNWY (SEQ ID NO: 1), YDYNLY (SEQ ID NO: 2), FDYNFY (SEQ ID NO: 3), FDYNLY (SEQ ID NO: 4), FDYNWY (SEQ ID NO: 5), YDWNLY (SEQ ID NO: 6), YDWHLY (SEQ ID NO: 7) and WDYNLY (SEQ ID NO: 8), extracted from organisms such as aquatic organisms and moss and methods of using same. Other sequences are described below.

One of the major concerns in medicine is microbial biofilm formation. In humans, biofilms are a cause of systemic infections (e.g., nosocomial infections) and are a major concern when introducing products into the body (e.g., contact lenses, central venous catheters, mechanical heart valves and pacemakers).

Biofilms are also a problem in many industries including the food, pharmaceutical, paint, water, shipping and engineering industries causing, amongst a wide range of negative effects, accelerated corrosion in industrial systems, oil souring and biofouling. For example, biofouling may be caused by the adhesion of organisms to any surface in a marine or freshwater environment, including cooling towers, water pipes and filters in cooling or desalinization installations, irrigation and power stations, and membranes, such as those used in wastewater and desalinization systems. Biofouling also occurs in aquaculture systems in fish farms.

Furthermore the commercial shipping fleets of the world consume approximately 300 million tones of fuel annually. Without antifouling measures, that fuel consumption would increase by as much as 40%, equivalent to an extra 120 million tones of fuel annually. The economic cost of this was estimated as about $7.5 billion in 2000; a more recent estimate is $30 billion.

Biofilms are very difficult to eliminate Since microbes growing within are highly organized and can withstand hostile environments, such as high temperatures and antimicrobial agents (e.g., antibiotics).

Marine and fresh water plants and organisms including soft bodied water invertebrates, fish and moss are surrounded by broad spectrum species of microbial organisms. Since such plant and organisms lack specific immunity, they produce several factors which can prevent microbial colonization on their body surface.

The most "sensitive" organisms are invertebrates belong to the phylum cnidaria that include the sea anemones, corals, jellyfish, hydroids, medusae, and sea fans. Such soft bodied organism, which lack physical protection such as scales or shells, use proteins and secondary metabolites to protect themselves from the microbial environment surrounding them.

It has been previously reported that marine organisms (e.g. sponges) produce secondary metabolites that exhibit antibacterial and antifungal activities [Amade et al., supra]. Moreover, sea anemones (e.g., Actinia equina) have been shown to produce toxic, pore forming peptides (i.e., equinatoxins), which lyse and kill eukaryotic cells similarly to other small antimicrobial peptides [Anderluh et al., supra].

Although it is known in the art that the full length sequences of various proteins are related to their cytolysic function, the specific peptides responsible for the cytolysic effect have not been previously identified.

The present inventors have demonstrated that several active fractions obtained from sea anemones using liquid chromatography separations show a high level of prevention of microbial adherence to abiotic surfaces. The sea anemone includes 46 families that can be found in water sources around the world. Most sea anemones are sessile, with a specialized foot used to anchor them in soft substrates, or attach themselves to rocks and corals. The anti-adhesive activity was demonstrated with several species of sea anemone belonging to different genera: Actinia equine, Aiptasia and Anemonia. The N terminus region of anemone cytotoxin has been shown to be involved in the cytotoxic effect [Ref: Kristan K, Podlesek Z, Hojnik V, Gutierrez-Aguirre I, Gunčar G, Turk D, Gonzalez-Manas J M, Lakey J H, Maček P, Anderluh G (2004): Pore formation by equinatoxin, an eukaryotic pore-forming toxin, requires a flexible N-terminal region and a stable beta sandwich, J Biol Chem, 279(45):46509-46517]. A protein having some resemblance to the C terminus region of anemone cytotoxin, which region is not involved in cytotoxicity, has also been identified in fish by the present inventors. This protein has a highly conserved region, with unknown function, which is also a Trp-rich domain, and may be important for binding of the protein to lipid membrane. The present inventors have also found this region in the moss Physcomitrella patens.

The present inventors therefore hypothesized that this region provides a peptide which is highly effective in prevention in biofilm formation, while being devoid of cytotoxic activity. The present inventors have characterized and isolated a natural peptide comprising a sequence selected from the group consisting of YDYNWY (SEQ ID NO: 1), YDYNLY (SEQ ID NO: 2), FDYNFY (SEQ ID NO: 3), FDYNLY (SEQ ID NO: 4), WDYNLY (SEQ ID NO: 8), FDYNWY (SEQ ID NO: 5), YDWNLY (SEQ ID NO: 6) and YDWHLY (SEQ ID NO: 7), having highly effective anti-biofilm properties.

According to some embodiments, the peptide comprises part of a sequence comprising 10 up to about 30, up to about 40, or up to about 50 amino acids.

According to some embodiments, the peptide is selected from the group consisting of LFSVPYDYNWYSNWW (SEQ ID NO: 9), FSVPYDYNLYSNWW (SEQ ID NO: 10), MFSVPFDYNFYSNWW (SEQ ID NO: 11), MFSVPFDYNLYSNWW (SEQ ID NO: 12), MFSVPFDYNLYTNWW (SEQ ID NO: 13), MWSVPFDYNLYSNWW (SEQ ID NO: 14), MFSVPWDYNLYKNWF (SEQ ID NO: 15), MFSVPFDYNLYKNWL (SEQ ID NO: 16), MFSVPFFDYNWYSNWW (SEQ ID NO: 17), LFSVPFDYNLYSNWW (SEQ ID NO: 18), LFSVPYDYNWYSNWW (SEQ ID NO: 9), MASIPYDWNLYQSWA (SEQ ID NO: 19), MASIPYDWNLYSAWA (SEQ ID NO: 20), and MASIPYDWHLYNAWA (SEQ ID NO: 21). As is shown herein below and in the Examples section which follows, the present inventors have identified an active fraction extracted from Aiptesia pulchella anemone, using tandem mass spectroscopy (MS/MS) analysis.

The present inventors used the clustaLW program to identify biologically meaningful 20 multiple sequence alignments of several anemone cytotoxin proteins and identify an anemone cytotoxin universal primer for use in a polymerase chain reaction (PCR). Amplification of a 250 bp region of cytotoxin proteins from two different anemones, aiptesia and anemonia viridansm, of sequence Eqt-F: GTR TCG ACA ACG AGT CRG G (SEQ ID NO: 22) and Eqt-R252: TGA CAT YCC ACC AGT TGC TG (SEQ ID NO: 23), respectively, was achieved. Translation of these regions to peptides, and BlastX comparison to the genebank, showed that these regions are part of the conserved domain of anemone cytotoxin. As discussed in greater detail in the Examples section below, and shown in FIGS. 5 to 8, the present inventors compared the activities of a number of synthetic peptides from anemones and moss, and found that these peptides prevented the formation of biofilm [FIGS. 6 and 8 to 12], but did not kill or inhibit growth of bacteria [FIGS. 5 and 7].

The anti-adhesive effect was demonstrated on several bacterial species (FIG. 10), which led the present inventors to conclude that the active materials are not species specific but active against a broad range of microbial species.

The conserved peptide region has been identified, for example, in the following natural proteins: (SEQ ID NOS 24-31, respectively, in order of appearance)

```
LFSVPYDYNWYSNWW  EqT-IV

FSVPYDYNLYSNWW   Actinoporin Or-A

MFSVPFDYNFYSNWW  HMg III from Heteractis magnifica

MFSVPFDYNLYSNWW  Avt-I RTX-A

MFSVPFDYNLYTNWW  Pstx20

MWSVPFDYNLYSNWW  Physcomitrella patens

MFSVPWDYNLYKNWF  Danio rerio

MFSVPFDYNLYKNWL  Tetraodon nigroviridis
```

Optionally and preferably, the peptide of the present invention comprises the sequence CMFSVPFDYNWYSNWWC (SEQ ID NO: 32). Optionally and preferably, the peptide of the present invention is comprised in a protein having from about 100 to about 300 amino acids.

Without wishing to be limited by a single hypothesis, based on the 3-dimensional structure of 2 anemone cytotoxin (equinatoxin and Sticholysin), as shown in FIGS. 1-4, the active region faces outwards.

FIGS. 1 and 2 shows the crystal structure of the 1GWY chains A and B, respectively, of cytolysin sticholysin Ii. FIG. 3 shows the structure of the 1KD6 chain A of the eukaryotic pore-forming cytolysin equinatoxin FIG. 4 demonstrates the 3-dimensional construct of an equinatoxin mutant, having three cysteines introduced at positions 8, 18 and 69 (1TZQ Chain A). This mutant has been previously shown not to be hemolytically active (Kristan K, Podlesek Z, Hojnik V, Gutierrez-Aguirre I, Guncar G, Turk D, Gonzalez-Manas J M, Lakey J H, Macek P, Anderluh G (2004): Pore formation by equinatoxin, an eukaryotic pore-forming toxin, requires a flexible N-terminal region and a stable beta sandwich, J Biol Chem. 279 (45):46509-46517). The protein thus lost its cytotoxicity, but was still active against bacterial adherence.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

According to one aspect of the present invention, there is provided a composition comprising an isolated natural peptide, the peptide comprising a sequence selected from the group consisting of YDYNWY (SEQ ID NO: 1), YDYNLY (SEQ ID NO: 2), FDYNFY (SEQ ID NO: 3), FDYNLY (SEQ ID NO: 4), WDYNLY (SEQ ID NO: 8), FDYNWY (SEQ ID NO: 5), YDWNLY (SEQ ID NO: 6) and YDWHLY (SEQ ID NO: 7).

According to an additional aspect of the present invention there is provided a method of preventing adhesion of a single cell organism to a surface, the method comprising contacting the cell with a composition of comprising an isolated natural peptide comprising a sequence selected from the group consisting of YDYNWY (SEQ ID NO: 1), YDYNLY (SEQ ID NO: 2), FDYNFY (SEQ ID NO: 3), FDYNLY (SEQ ID NO: 4), WDYNLY (SEQ ID NO: 8), FDYNWY (SEQ ID NO: 5), YDWNLY (SEQ ID NO: 6) and YDWHLY (SEQ ID NO: 7), thereby preventing adhesion of a cell to a surface.

According to some embodiments of the present invention, there is preferably provided a domain which comprises at least one of the above peptides and which is effective against cell adhesion to a surface. More preferably, the domain is included as part of a protein. Optionally and most preferably, the domain exhibits anti-adhesive behavior, for example for the prevention of formation and/or treatment of a biofilm, but does not exhibit cytotoxic behavior.

A non-limiting selection of exemplary domains is provided in the table below.

| Domain sequence | Species |
| --- | --- |
| LFSVPYDYNWYSNWW (SEQ ID NO: 24) | EqT-IV |
| FSVPYDYNLYSNWW (SEQ ID NO: 25) | Actinoporin Or-A |
| MFSVPFDYNFYSNWW (SEQ ID NO: 26) | HMg III from *Heteractis magnifica* |
| MFSVPFDYNLYSNWW (SEQ ID NO: 27) | Avt-I RTX-A |
| MFSVPFDYNLYTNWW (SEQ ID NO: 28) | Pstx20 |
| MWSVPFOYNLYSNWW (SEQ ID NO: 29) | *Physcomitrella patens* |
| MFSVPWDYNLYKNWF (SEQ ID NO: 30) | *Danio rerio* |
| MFSVPFDYNLYKNWL (SEQ ID NO: 31) | *Tetraodon nigroviridis* |

Further exemplary sequences are described herein, as being related to the following sequence:

```
                                          (SEQ ID NO: 33)
MSRLIIVFIVVTMICSATALPSKKIIDEDEEDEKRSADVAGAVIDGASL

SFDILKTVLEALGNVKRKIAVGVDNESGKTWTALNTYFRSGTSDIVLPH

KVPHGKALLYNGQKDRGPVATGAVGVLAYLMSDGNTLAVLFSVPYDYNW

YSNWWNVRIYKGKRRADQRMYEELYYNLSPFRGDNGWHTRNLGYGLKSR

GFMNSSGHAILEIHVSKA.
```

This sequence has the GenBank accession identifier: >gi|48428895|sp|P61914.1|ACTP2_ACTEQ Equinatoxin-2 precursor (Equinatoxin II) (EqT II) (EqTII) *Actinia equine* and is 214 aa in length. This sequence is also optionally an exemplary sequence according to the present invention. Positions 38-213 of this sequence hit the annotated domain pfam06369, Anemone_cytotox, Sea anemone cytotoxic protein; therefore, this portion of the above sequence is also optionally an exemplary sequence according to the present invention.

In some embodiments, the present invention also includes any related sequence to the above sequence thereof. Such related sequences may optionally be found by running any type of sequence comparison software, including but not limited to BLASTP. Below are provided representative hits from selected taxa and their alignments to EqtII (the above sequence):

1. Sea Anemones—
1a. *Stichodactyla helianthus*

>gi|2815496|sp|P07845.2|ACTP2_STOHE Sticholysin-2 (Sticholysin II) (StnII) (Cytolysin St II) (Cytolysin III) (Cytotoxin)

```
                                          (SEQ ID NO: 34)
ALAGTIIAGASLTFQVLDKVLEELGKVSRKIAVGIDNESGGTWTALNAY

FRSGTTDVILPEFVPNTKALLYSGRKDTGPVATGAVAAFAYYMSSGNTL

GVMFSVPFDYNWYSNWWDVKIYSGKRRADQGMYEDLYYGNPYRGDNGWH

EKNLGYGLRMKGIMTSAGEAKMQIKISR
```

Alignment:
>sp|P³07845.2|ACTP2_STOHE Sticholysin-2 (Sticholysin II) (StnII) (Cytolysin St II) (Cytolysin III) (Cytotoxin)
Length=175
Score=253 bits (646), Expect=8e-66, Method: Composition-based stats.
Identities=118/176 (67%), Positives=144/176 (81%), Gaps=1/176 (0%)

```
Query  38  DVAGAVIDGASLSFDILKTVLEALGNVKRKIAVGVDNESGKTWTALNTYFRSGTSDIVLP   97
              +AG +I GASL +F +L VLE LG V RKIAVG+DNESG TWTALN YFRSGT+D++LP
Sbjct   1  ALAGTIIAGASLTFQVLDKVLEELGKVSRKIAVG1DNESGGTWTALNAYFRSGTTDVILP   60

Query  98  HKVPHGKALLYNGQKDRGPVATGAVGVLAYLMSDGNTLAVLFSVPYDYNWYSNWWNVRIY  157
              VP+ KALLY+G+KD GPVATGAV AY MS GNTL V+FSVP+DYNWYSNWW+V+IY
Sbjct  61  EFVPNTKALLYSGRKDTGPVATGAVAAFAYYMSSGNTLGVMFSVPFDYNWYSNWWDVKIY  120

Query 158  KGKRRADQRMYEELYYNLSPFRGDNGWHTRNLGYGLKSRGFMNSSGHA1LE1HVSK      213
              GKRRADQ MYE+LYY +P+RGDNGWH +NLGYGL+ +G M S+G A ++1 +S+
Sbjct 121  SGKRRADQGMYEDLYYG-NPYRGDNGWHEKNLGYGLRMKG1MTSAGEAKMQ1K1SR       175
```

(The above "Query" and "Sbjt" sequences disclosed as SEQ ID NOS 35 and 34, respectively.)

2. Bony Fish
2a. *Danio rerio*

>gi|125821212|ref|XP_001342650.1|PREDICTED: hypothetical protein [*Danio rerio*]
(SEQ ID NO: 36)
MTESAEAVAANVSSRRHATVEITNLTNNYCFLNPKVYLENGETSNPPQP

TVRPLKTEVCTFSKSAAHATGSVGVLTYDLFERRRNDYTETLAIMFSVP

WDYNLYKNWFAVGIYPKGKECDQALYKEMYYQKNQHGFVREEANGSGIN

FEGKNLD1RATMCPMGRAIVKVEVWDKLLSPMAQMDC

Alignment:
>ref|XP_001342650.1|UniGene infoGene info PREDICTED: hypothetical protein [*Danio rerio*]
Length=184
GENE ID: 100002992 apn1|actinoporin-like protein [*Danio rerio*]
Score=199 bits (505), Expect=1e-49, Method: Composition-based stats.
Identities=49/167 (29%), Positives=73/167 (43%), Gaps=12/167 (7%)

```
Query  58  LEALGNVKRKIAVGVDNESG-KTWTALNTYFRSGTSDIVLPHKVPHGKALLYNGQKDRGP  116
              + A + +R V + N + + Y +G + V K + K
Sbjct   8  VAANVSSRRHATVEITNLTNNYCFLNPKVYLENGETSNPPQPTVRPLKTEVCTFSKSAAH   67

Query 117  VATGA VGVLAYLMSD------GNTLAVLFSVPYDYNWYSNWWNVRIYKGKRRADQRMYEE  170
              ATG+VGVL Y + + TLA++FSVP+DYN Y NW+ V IY + DQ +Y+E
Sbjct  68  ATGSVGVLTYDLFERRRNDYTETLAIMFSVPWDYNLYKNWFAVGIYPKGKECDQALYKE   126

Query 171  LYYNLSPF----RGDNGWHTRNLGYGLKSRGFMNSSGHAILEIHVSK              213
              +YY + VN G L R M G AI+++ V
Sbjct 127  MYYQKNQHGFVREEANGSGINFEGKNLDIRATMCPMGRAIVKVEVWD              173
```

(The above "Query" and "Sbjct" sequences disclosed as SEQ ID NOS 37-38, respectively.)

2b. *Tetraodon nigroviridis*

>gi|47218822|emb|CAG02807.1|unnamed protein product [*Tetraodon nigroviridis*]
(SEQ ID NO: 39)
MESAEAVAADVSRSRSVTIEISNLTKNYCLINPRVYLESGETYNPPQPT

VRPLMTEVCTFSKSSGIPTGSVGVLTYELLERRSTMLPETLAIMFSVPY

DYSFYNNWFAVGIYETGTKCNEGLYKQMYNEKKQAEHGFVREKANGSGI

NYVGGNLDIRATMNPLGKAIMKVEVWDAFFPFSE

Alignment:
>emb|CAG02807.1|unnamed protein product [*Tetraodon nigroviridis*]
Length=181
Score=192 bits (489), Expect=1e-47, Method: Composition-based stats.
Identities=46/170 (27%), Positives=76/170 (44%), Gaps=14/170 (8%)

```
Query  58  LEALGNVFRKIAVGVDNES-GKTWTALNTYFRSGTSDIVLPHKVPHGKALLYNGQKDRGP  116
              + A + R + + + N + Y SG + V + KG
Sbjct   7  VAADVSRSRSVTIEISNLTKNYCLINPRVYLESGETYNPPQPTVRPLMTEVCTFSKSSG   65

Query 117  VATGAVGVLAYLMSD------GNTLAVLFSVPYDYNWYSNWWNVRIYKGKRRADQRMYEE  170
              + TG+VGVL Y + + TLA++FSVPYDY++Y+NW+ V IY+ + ++ +Y++
```

```
Sbjct  66 IPTGSVGVLTYELLERRSTMLPETLAIMFSVPYDYSFYNNWFAVGIYETGTKCNEGLYKQ 125

Query 171 LYYNLSPF------RGDNGWHTRNLGYGLKSRGFMNSSGHAILEIHVSKA          214
          +Y NG +G L R MN G AI+++ V A
Sbjct 126 MYNEKKQAEHGFVREKANGSGINYVGGNLDIRATMNPLGKAIMKVEVWDA           175
```

(The above "Query" and "Sbjct" sequences disclosed as SEQ ID NOS 40-41, respectively.)

3. Mosses
3a. *Physcomitrella patens*

>gi|168060237|ref|XP_001782104.1|predicted protein [*Physcomitrella* patens subsp. patens]
(SEQ ID NO: 42)
MVVHLIAMGLRYSETIMKTARMAEAIIPAAELSIKTLQNIVEGITGVDRK

IAIGFKNLTDYTLENLGVYFNSGSSDRSIAYKINAQEALLFSARKSDHTA

RGTVGTFSYYIQDEDKTVHVMWSVPFDYNLYSNWWNIAVVDGRQPPDSNV

HDNLYNGSGGMPYPNKPDQYINNEQKGFHLFGSMTNNGQATIEVELKKA

>ref|XP_001782104.1|Gene info predicted protein [*Physcomitrella patens* subsp. *patens*]
gb|EDQ53098.1|Gene info predicted protein [*Physcomitrella patens* subsp. *patens*]
Length=199
GENE ID: 5945292 PHYPADRAFT_61094|hypothetical protein [*Physcomitrella patens* subsp. *patens*]
Score=230 bits (586), Expect=7e-59, Method: Composition-based stats.
Identities=63/183 (34%), Positives=101/183 (55%), Gaps=4/183 (2%)

```
Query  35 RSADVAGAVIDGASLSFDILKTVLEALGNVKRKIAVGVDNESGKTWTALNTYFRSGTSDI   94
          ++A +A A+I A LS L+ ++E + V RKIA+G N + T L YF SG+SD
Sbjct  18 KTARMAEAIIPAAELSIKTLQNIVEGITGVDRKIAIGFKNLTDYTLENLGVYFNSGSSDR  77

Query  95 VLPHKVPHGKALLYNGQKDRGPVATGAVGVLAYLMSD-GNTLAVLFSVPYDYNWYSNWWN 153
          + +K+ +ALL++ +K A G VG +Y + D T+ V++SVP+DYN YSNWWN
Sbjct  78 SIAYKINAQEALLFSARKSDH-TARGTVGTFSYYIQDEDKTVHVMWSVPFDYNLYSNWWN 136

Query 154 VRIYKGKRRADQRMYEELYYNL-SPFRGDNGWHTRNLGYGLKSRGFMNSSGHAILEIHV  211
          + + G++ D +++ LY P+ + N G G M ++G A +E+ +
Sbjct 137 IAVVDGRQPPDSNVHDNLYNGSGGMPYPNKPDQYINNEQKGFHLFGSMTNNGQATIEVEL 196

Query 212 SKA                                                        214
          KA
Sbjct 197 KKA                                                         199
```

(The above "Query" and "Sbjct" sequences disclosed as SEQ ID NOS 43-44, respectively.)

4. Birds
4a. *Gallus gallus*

>gi|118129726|ref|XP_001231839.1|PREDICTED: hypothetical protein isoform 1 [*Gallus gallus*]
(SEQ ID NO: 45)
MPPKEKKENDKPCNDNCQPKPQGKGVESLMKNIDVCRSVGLEIINRTRT

VTLTDFRSYCFSGKIVTTLPFEIGPDSKGICIFAKTPYSLRGSVGTVVC

KADTFFLAITFSNPYDYILYKIEFALEIFTEPNHLGNLGDVFSKMMKSK

PYCGSSLFQRAVLESEHETLEVSKGSIRVQAKMSNNRKAILKVQVEDMD

PPPYSKGM

>ref|XP_001231839.1|UniGene infoGene info PREDICTED: hypothetical protein isoform 1 [*Gallus gallus*]
Length=204
GENE ID: 769729 LOC7697291 hypothetical protein LOC769729 [*Gallus gallus*]
Score=150 bits (378), Expect=9e-35, Method: Composition-based stats.
Identities=33/172 (19%), Positives=63/172 (36%), Gaps=22/172 (12%)

```
Query  58 LEALGNVKRKIAVGVDNES-GKTWTALNTYFRSGTSDIVLPHKVPHGKALLYNGQKDRGP 116
          L +V R + + N + T T +Y SG LP ++ + K
Sbjct  29 LMKNIDVCRSVGLEIINRTRTVTLTDFRSYCFSGKIVTTLPFEIGPDSKGICIFAKTP-Y  87

Query 117 VATGAVGVLAYLMSDGNTLAVLFSVPYDYNWYSNWWNVRIYKGKRRADQ-----RMYEEL 171
```

```
                V+VG +  +D LA+ FS PYDY Y + + 1+ + ++ ++
Sbjct  88  SLRGSVGTVVCK-ADTFFLAITFSNPYDYILYKIEFALEIF---TEPNHLGNLGDVFSKM  143

Query 172  YYNLSPFRG----------DNGWHTRNLGYGLKSRGFMNSSGHAILEIHVSK          213
           P+ G ++ +  M+++ AIL++ V
Sbjct 144  MK-SKPYCGSSLFQRAVLESEHETLEVSKGSIRVQAKMSNNRKAILKVQVED          194
```

(The above "Query" and "Sbjct" sequences disclosed as SEQ ID NOS 37 and 46, respectively.)

5. Platypus

5a. *Ornithorhynchus anatinus*

```
>gi|149491241|ref|XP_001516906.1|PREDICTED:
hypothetical protein [Ornithorhynchus anatinus]
                                          (SEQ ID NO: 47)
MAQTIEHLVHEVEAGRCVGIEITNTTNMTFRSPRTFCFSGHTLTPPTPI

IHPNNAGFCIFVKRKFSLRGSVGLLVYEIEDQTLAIMFSNPFDYNFFKV

EFAVALSGYKEETQDLKAFFELLYHEKQKGWLKMAKEKLCECQCPVSLE

NNGIRVTATMSNNAKAIIKLSSPDAKPPEGDVADVQPTTVRRPNPPPFP

SPRPRIGSDLTGDQLATLDFESGK
```

>ref|XP_001516906.1|Gene info PREDICTED: hypothetical protein [Ornithorhynchus anatinus]

Length=220

GENE ID: 100086848 LOC100086848|hypothetical protein LOC100086848 [Ornithorhynchus anatinus]

Score=168 bits (426), Expect=2e-40, Method: Composition-based stats.

Identities=36/167 (21%), Positives=69/167 (41%), Gaps=12/167 (7%)

```
Query  58  LEALGNVKRKIAVGVDNESGKTWTALNTYFRSGTSDIVLPHKVPHGKALLYNGQKDRGPV  117
           L R + + + N + T+ + T+ SG + + A K R
Sbjct   8  LVHEVEAGRCVGIEITNTTNMTFRSPRTFCFSGHTLTPPTPIIHPNNAGFCIFVK-RKFS   66

Query 118  ATGAVGVLAYLMSDGNTLAVLFSVPYDYNWYSNWWNVRI-YKGKRRADQRMYEELYYNL   175
           G+VG+L Y + D  TLA++FS P+DYN++ + V + YK + + + +E LY+
Sbjct  67  LRGSVGLLVYEIED-QTLAIMFSNPFDYNFFKVEFAVALSGYKEETQDLKAFFELLYHEK  125

Query 176  --------SPFRGDNGWHTRNLGYGLKSRGFMNSSGHAILEIHVSKA               214
           + G++ M+++ AI+++ A
Sbjct 126  QKGWLKMAKEKLCECQCPVSLENNGIRVTATMSNNAKAIIKLSSPDA                172
```

(The above "Query" and "Sbjct" sequences disclosed as SEQ ID NOS 48-49, respectively.)

As used herein, the term "isolated" refers to a composition that has been removed from its in-vivo location (e.g. aquatic organism or moss). Preferably the isolated compositions of the present invention are substantially free from other substances (e.g., other proteins that do not comprise antiadhesive effects) that are present in their in-vivo location (i.e. purified or semi-purified).

As used herein the phrase "aquatic organism" refers to an organism living in a water environment (marine or freshwater) such as for example a fish or a sessile aquatic organism.

As used herein, the phrase "sessile aquatic organism" refers to an aquatic organism which is not freely moving for at least some a part of its life cycle. Aquatic sessile organisms are usually permanently attached to a solid substrate of some kind, such as to a rock or the hull of a ship due to physical anchorage to the substrate, or for any other reason (e.g. stone fish).

Exemplary sessile organisms include, but are not limited to, sessile cnidarians such as corals, sea anemones (e.g. *Actinia equine* and *Aiptasia pulchella*), sea pens, aquatic sessile larva (e.g., jellyfish larva), tube dwelling anemones and hydroids (e.g. *Chlorohydra viridissima* and *Hydra vulgaris*).

Exemplary fish that may be used according in embodiments of the present invention are preferably those dwelling in shallow waters or those that hide at the bottom layer of the ocean, sometimes in holes or caves. Such fish include eel and catfish.

As used herein the phrase "moss" refers to a non-vascular plant of the bryophyta division, including any of the classes takakiposida, sphyagnopsida, andreaeopsida, anderaeobryopsida, polytirchopsida, or bryopsisa.

The moss may comprise, for example, *physcomitrella patens, Funaria hygrometrica*; Eukaryota; Viridiplantae; Streptophyta; Embryophyta; Bryophyta; Moss Superclass V; Bryopsida; Funariidae; Funariales; Funariaceae; or *Physcomitrella*.

The compositions of the present invention may also be expressed in-vivo using genetic engineering techniques (e.g. using transgenic aquatic sessile organisms).

According to some embodiments of the present invention, the compositions of the present invention are devoid of cytotoxic or cytostatic activity, e.g. they are not bactericidal or bacteristatic.

According to some embodiments of the present invention, the compositions of the present invention are resistant to lyophilization—e.g. their activities are preserved following freeze drying.

As used herein the phrase "single cell organism" refers to a unicellular organism also termed a microorganism or a microbe. The single cell organism of the present invention can be a eukaryotic single cell organism (e.g., protozoa or fungi for example yeast) or a prokaryotic single cell organism (e.g., bacteria or archaea). The single cell organisms of the present invention may be in any cellular environment, such as for example, in a biofilm, as isolated cells or as a cell suspension.

As used herein the term "biofilm" refers to an extracellular matrix In which microorganisms are dispersed and/or form colonies. The biofilm typically is made of polysaccharides and other macromolecules.

Exemplary bacterial cells, whose adhesion may be prevented according to the method of the present invention, include gram positive bacteria and gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecal is, Enterococcus faecium, Erysipelothrix rhusiopathiae, Eubacterium* spp., *Gardnerella vaginalis, Gemella morbillorum, Leuconostoc* spp., *Mycobacterium abscessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Sarcina lutea, Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus, Acinetobacter baumannii, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella pneumoniae, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteuretlaniultocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Shigella sonnei, Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis*.

The term "fungi" as used herein refers to the heterotrophic organisms characterized by the presence of a chitinous cell wall, and in the majority of species, filamentous growth as multicellular hyphae. Representative fungi whose adhesion may be prevented according to the method of the present invention include *Candida albicans, Saccharomyces cerevisiae, Candida glabrata, Candida parapsilosis* and *Candida dubliniensis*.

As used herein the phrase "preventing adhesion" refers to reducing or eliminating cell attachment to a surface (e.g. by reducing the rate of growth on a surface). Preferably, the compositions of the present invention prevent cell adhesion by as much as 10%, more preferably by 20%, more preferably by 30%, more preferably by 40%, more preferably by 50%, more preferably by 60%, more preferably by 70%, more preferably by 80%, more preferably by 90% and most preferably by 100% as measured by a cell adhesion assay. Exemplary cell adhesion assays are described herein below and in the Examples section that follows. It will be appreciated that the compositions of the present invention may also be capable of preventing cell aggregation (i.e. cell aggregation not to a surface).

The present invention contemplates prevention of cellular adhesion to a wide variety of surfaces including fabrics, fibers, foams, films, concretes, masonries, glass, metals, plastics, polymers, and like.

According to one embodiment, the surface is comprised in a device that is susceptible to biofilm formation. Exemplary devices whose surfaces are contemplated by the present invention include, but are not limited to, vessel hulls, automobile surfaces, air plane surfaces, membranes, filters, and industrial equipment. The surface may also be comprised in medical devices, instruments, and implants. Examples of such medical devices, instruments, and implants include any object that is capable of being implanted temporarily or permanently into a mammalian organism, such as a human. Representative medical devices, instruments, and implants that may be used according to the present invention include, for example, central venous catheters, urinary catheters, endotracheal tubes, mechanical heart valves, pacemakers, vascular grafts, stents and prosthetic joints. Methods of preventing cell attachment to medical devices and further examples thereof are described herein below.

According to another embodiment the surface is comprised in a biological tissue, such as for example, mammalian tissues e.g. the skin.

As mentioned, the method of the present invention is effected by contacting the cell with a composition from an organism capable of preventing adhesion of the cell to a surface.

As used herein the term "contacting" refers to the positioning of the compositions of the present invention such that they are in direct or indirect contact with the adhesive cells in such a way that the active agent comprised within is able to prevent adhesion of cells thereto. Thus, the present invention contemplates both applying the compositions of the present invention to a desirable surface and/or directly to the adhesive cells. The contacting may be effected in vivo (i.e. within a mammalian body), ex vivo (i.e. in cells removed from the body) and/or in vitro (i.e. outside a mammalian body).

Contacting the compositions with a surface can be effected using any method known in the art including spraying, spreading, wetting, immersing, dipping, painting, ultrasonic welding, welding, bonding or adhering. The compositions of the present invention may be attached as monolayers or multiple layers.

According to one embodiment, the compositions of the present invention may be comprised in a whole living organism. For example, the present invention contemplates adding live aquatic organisms to an underwater environment such that they are able to contact a surface and/or cells adhered thereto (e.g. underwater pipes, ship hull) preventing microorganism adhesion thereto. It will be appreciated that the active agent may be secreted from the aquatic organism. In this case, the aquatic organism does not have to be in direct contact with the surface or microorganism cells, but in sufficient proximity such that the active agent is able to diffuse to its site of action. Thus, the compositions of the present invention may be secreted into water and used in water purification treatments such as for example desalination of sea water or brackish water.

According to a further aspect of the present invention, there is provided a pharmaceutical composition comprising a pharmaceutically acceptable carrier or diluent and as an active ingredient a peptide isolated from an isolated natural peptide, said peptide comprising a sequence selected from the group consisting of YDYNWY (SEQ ID NO: 1), YDYNLY (SEQ ID NO: 2), FDYNFY (SEQ ID NO: 3), FDYNLY (SEQ ID NO: 4), WDYNLY (SEQ ID NO: 8), FDYNWY (SEQ ID NO: 5), YDWNLY (SEQ ID NO: 6) and YDWHLY (SEQ ID NO: 7), or any other sequence as described herein.

According to other embodiments of the present invention, the above peptides may optionally be altered so as to form non-peptide analogs, including but not limited to replacing one or more bonds with less labile bonds, cyclization (described in greater detail below) and the like. Additionally or alternatively, a peptide may optionally be converted to a small molecule through computer modeling, as described for example in PCT Application No. W0/20071147098, hereby incorporated by reference as if fully set forth herein.

A "peptidomimetic organic moiety" can optionally be substituted for amino acid residues in a peptide according to the present invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the composition at least substantially retains its physiological activity as compared to the native peptide according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875 5880 (1988)); isosteres of amide bonds (Jones et al., Tetrahedron Lett. 29: 3853 3856 (1988)); LL 3 amino 2 propenidone 6 carboxylic acid (LL Acp) (Kemp et al., J. Org. Chem. 50:5834 5838 (1985)). Similar analogs are shown in Kemp et al., Tetrahedron Lett. 29:5081 5082 (1988) as well as Kemp et al., Tetrahedron Lett. 29:5057 5060 (1988), Kemp et al., Tetrahedron Lett. 29:4935 4938 (1988) and Kemp et al., J. Org. Chem. 54: 109 115 (1987). Other suitable but exemplary peptidomimetics are shown in Nagai and Sato, Tetrahedron Lett. 26:647650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323 333 (1990); Garvey et al., J. Org. Chem. 56:436 (1990). Further suitable exemplary peptidomimetics include hydroxy 1,2,3,4 tetrahydroisoquinoline 3 carboxylate (Miyake et al., J. Takeda Res. Labs 43:53 76 (1989)); 1,2,3,4 tetrahydro-isoquinoline 3 carboxylate (Kazmierski et al., J. Am. Chem. Soc. 133: 2275 2283 (1991)); histidine isoquinolone carboxylic acid (HIC) (Zechel et al., Int. J. Pep. Protein Res. 43 (1991)); (2S,3S) methyl phenylalanine, (2S,3R) methyl phenylalanine, (2R,3S) methyl phenylalanine and (2R,3R) methyl phenylalanine (Kazmierski and Hruby, Tetrahedron Left. (1991)).

Exemplary, illustrative but non-limiting non-natural ammo acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

In the present invention any part of a peptide may optionally be chemically modified, i.e. changed by addition of functional groups. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to anyone of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification," when referring to a peptide according to the present invention, refers to a peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

According to some embodiments of this aspect of the present invention, there is provided a method of preventing or treating a pathogen infection in a subject in need thereof, the method comprising administering to the subject a therapeutically effective amount of the pharmaceutical composition, thereby treating or preventing the pathogen infection.

According to alternative embodiments of this aspect of the present invention, there is provided a method of preventing attachment of exogenous bacteria to the gastrointestinal tract.

The mammalian gastrointestinal tract contains a wide variety of indigenous microflora, which provide resistance to colonization by enteric pathogen. In return for providing the host with enhanced defense against pathogens, the indigenous microflora gain access to a nutrient-enriched, stable environment, and thereby enter a symbiotic relation with the host's intestinal tract.

Symbiotic bacteria attach to the gastrointestinal epithelium in humans by high-affinity, receptor-mediated attachment. In contrast, exogenous bacteria attach to the epithelium by a low-affinity mechanism. Without wishing to be limited by a single hypothesis, the compositions of the present invention are expected to selectively prevent or decrease this low-affinity attachment, thereby preventing the initial step of biofilm formation.

The composition of the present invention is therefore useful for treatment or prevention of diseases of the gastrointestinal tract, such as, for example, Crohn's disease or ulcerative colitis, including, for example, collagneous colitis, lymphocytic colitis, ischaemic colitis, diversion colitis, infective colitis and Behcet's syndrome.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein the term "active ingredient" refers to the organism compositions (and agents purified therefrom) accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found In the latest edition of "Remington's Pharmaceutical Sciences," Mack Publishing Co., Easton, Pa., which is herein fully incorporated by reference and are further described herein below.

As mentioned, the pharmaceutical compositions of the present invention may be administered to a subject in need thereof in order to prevent or treat a pathogen infection.

As used herein the term "subject in need thereof" refers to a mammal, preferably a human subject.

As used herein the term "treating" refers to curing, reversing, attenuating, alleviating, minimizing, suppressing or halting the deleterious effects of a pathogen infection.

As used herein the phrase "pathogen infection" refers to any medical condition which is caused by a pathogenic organism. Examples of pathogen infections include, but are not limited to, chronic infectious diseases, subacute infectious diseases, acute infectious diseases, viral diseases, bacterial diseases, protozoan diseases, parasitic diseases, fungal diseases, *mycoplasma* diseases, archaea diseases and prion diseases.

According to one embodiment, the pathogen infection is caused by an organism capable of growing in or on a biofilm.

Examples of pathogen infections caused by microbial biofilms include native valve endocarditis (NVE), otitis media (OM), chronic bacterial prostatitis, cystic fibrosis (CF) and periodontitis. Additional pathogen infections that are not specifically attributed to biofilms include, but are not limited to urinary infections, female genital tract infections and pneumonia. Infections due to implantation of medical devices include vascular catheter infections, arterial prosthetic infections, infections of prosthetic heart valves, prosthetic joint infections, infections of central nervous system shunts, orthopedic implant infections, pacemaker and defibrillator infections, hemodialysis and peritoneal dialysis infections, ocular infections, urinary tract infections, infections of the female genital tract, infections associated with endotracheal intubation and tracheostomy and dental infections.

As used herein the phrase "pathogenic organism" refers to any single cell organism which is capable of causing disease, especially a living microorganism such as a bacteria or fungi. Preferably the pathogenic organism is capable of growing in or on a biofilm. Many common pathogenic organisms exist in mammals (e.g. humans) as biofilms and cause disease. These include, but are not limited to, *Mannheimia haemolytica* and *Pasteurella multocida* (causing pneumonia), *Fusobacterium necrophorum* (causing liver abscess), *Staphylococcus aureus* and *Pseudomonas aeruginosa* (causing wound infections), *Escherichia coli* and *Salmonella* spp (causing enteritis), *Staphylococcus aureus* and *Staphylococcus epidermidis* (causing OM), and Streptococci sp., Staphylococci sp., *Candida*, and *Aspergillus* sp. (causing NVE).

It will be appreciated that treatment of infectious diseases according to the present invention may be combined with other treatment methods known in the art (i.e., combination therapy). These include, but are not limited to, antimicrobial agents such as penicillins, cephalosporins, carbapenems, aminoglycosides, macrolides, lincomycins, tetracyclines, chloramphenicol, and griseofulvin.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For topical administration, the compositions of the present invention may be formulated as a gel, a cream, a wash, a rinse or a spray.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., an aquatic organism composition or a moss composition) effective to prevent, alleviate, or ameliorate symptoms of a pathogenic infection (e.g., fever) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.).

Dosage amount and administration intervals may be adjusted individual to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

As mentioned, medical devices and implants are commonly infected with opportunistic bacteria and other infectious microorganisms (e.g., fungi) in some cases necessitating the removal of implantable devices. Such infections can also result in illness, long hospital stays, or even death. The prevention of biofilm formation and infection of medical devices is therefore highly desirous.

Thus, the present invention also contemplates medical devices in which the above-described compositions are attached thereto.

As used herein the term "medical device" refers to any implant, instrument, apparatus, implement, machine, device or any other similar or related object (including any component or accessory), which is intended for use in the diagnosis, treatment, cure or prevention of disease or other conditions. Such medical device is intended for use in man or other animals and is anticipated to affect the structure or any function of the body. Such medical device does not achieve its primary intended purposes through chemical action and is not dependent upon being metabolized for the achievement of its primary intended purposes.

As used herein the term "implant" refers to any object intended for placement in a human body that is not a living tissue. The implant may be temporary or permanent. An implant can be an article comprising artificial components, such as catheters or pacemakers. Implants can also include naturally derived objects that have been processed so that their living tissues have been devitalized. As an example, bone grafts that have been processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies.

The present invention therefore envisions coating medical devices with the compositions of the present invention to prevent cell adherence thereto so as to reduce/eliminate any possible cell aggregation and biofilm formation known to occur following implantation. Device-related infections usually result from the introduction of microorganisms, primarily bacteria, during the device insertion or implantation procedure, or from attachment of blood-borne organisms to the newly inserted device and their subsequent propagation on its surface. Coating the medical device with the compositions of the present invention will therefore inhibit biofilm formation of one or more microbial species, will prevent medical device related infections, and consequently will reduce the need of antibiotic treatment or removal of the medical device from the subject.

Medical devices that may be coated according to the teachings of the present invention include, but not limiting to, artificial blood vessels, catheters and other devices for the removal or delivery of fluids to patients, artificial hearts, artificial kidneys, orthopedic pins, prosthetic joints, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, mechanical heart valves, artificial joints, artificial larynxes, otological implants), anastomotic devices, vascular catheter ports vascular stents, clamps, embolic devices, wound drain tubes, ocular lenses, dental implants, hydrocephalus shunts, pacemakers and implantable defibrillators, needleless connectors, voice prostheses and the like.

Another possible application of the compositions of the present invention is the coating of surfaces found in the medical and dental environment. Such surfaces include the inner and outer aspects of various instruments and devices, whether disposable or intended for repeated uses. Such surfaces include the entire spectrum of articles adapted for medical use, including without limitation, scalpels, needles, scissors and other devices used in invasive surgical, therapeutic or diagnostic procedures; blood filters. Other examples will be readily apparent to practitioners in these arts.

Surfaces found in the medical environment also include the inner and outer aspects of pieces of medical equipment, medical gear worn or carried by personnel in the health care setting. Such surfaces can include surfaces intended as biological barriers to infectious organisms in medical settings, such as gloves, aprons and faceshields. Commonly used materials for biological barriers are thermoplastic or polymeric materials such as polyethylene, dacron, nylon, polyesters, polytetrafluoroethylene, polyurethane, latex, silicone and vinyl. Other surfaces can include counter tops and fixtures in areas used for medical procedures or for preparing medical apparatus, tubes and canisters used in respiratory treatments, including the administration of oxygen, of solubilized drugs in nebulizers and of anesthetic agents. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

The compositions of the present invention can be used on the surface of or within these medical devices to provide long term protection against microorganism colonization and reduce the incidence of device-related infections. These compositions can also be incorporated in combination with an anti-microbial agent (e.g., antibiotic agent) into coatings for medical devices. Such a combination will sufficiently kill or inhibit the initial colonizing bacteria and prevent device-related infections as long as the substance is presented in an inhibitory concentration at the device-microbe interface.

The compositions of the present invention can be directly incorporated into the polymeric matrix of the medical device at the polymer synthesis stage or at the device manufacture stage. The compositions can also be covalently attached to the medical device polymer. These and many other methods of coating medical devices are evident to one of ordinary skill in the ant.

Additional surfaces that can be treated according to the teachings of the present invention include the inner and outer aspects of those articles involved in water purification, water storage and water delivery, and those articles involved in food processing. Thus the present invention envisions coating a solid surface of a food or beverage container to extend the shelf life of its contents.

Surfaces related to health can also include the inner and outer aspects of those household articles involved in providing for nutrition, sanitation or disease prevention. Thus, the compositions of the present invention can be used for removal of disease-causing microorganisms from external surfaces. These can include, for example food processing equipment for home use, materials for infant care, tampons, soap, detergents, health and skincare products, household cleaners and toilet bowls.

The surface may be also be laboratory articles including, but not limited to, microscopic slide, a culturing hood, a Petri dish or any other suitable type of tissue culture vessel or container known in the art.

The inventors of this application also envision the use of the compositions of the present invention as anti-fouling agents.

As used herein the term "anti-fouling agents" refers to the compounds used to protect underwater surfaces from attaching single cell organisms. These single cell organisms include microorganism such as bacteria and fungi.

These underwater surfaces include any water immersed surface, including ships'/boats's hulls (i.e., the body or frame of a ship or boat), submergence vehicles, navigational aids, screens, nets, constructions, floating or emplaced offshore platforms (e.g., docks), buoys, signaling equipment and articles which come into contact with sea water or salty water. Other underwater surfaces include structures exposed to sea water including pilings, marine markers, undersea conveyances like cabling and pipes, fishing nets, bulkheads, cooling towers, and any device or structure that operates submerged.

The compositions of the present invention can be incorporated into marine coatings to limit undesirable marine fouling. Thus, the anti-fouling agents of the present invention can be formulated so as not to contain toxic materials (such as heavy metals), and still retain their efficacy. The anti-fouling paint of the present invention may further contain binders(s), pigment(s), solvent(s) and additive(s).

Examples of solvents that may be used include aromatic hydrocarbons such as xylene and toluene; aliphatic hydrocarbons such as hexane and heptane, esters such as ethyl acetate and butyl acetate; amides such as N-methylpyrrolidone and N,N-dimethylformamide; alcohols such as isopropyl alcohol and butyl alcohol; ethers such as dioxane, THF and diethyl ether; and ketones such as methyl ethyl ketone, methyl isobutyl ketone and methyl isoamyl ketone. The solvents may be used alone or in combination thereof.

Examples of binders that may be used include alkyd resin, acrylic or vinyl emulsions, polyurethane resins, epoxy resins, silicone based resins, acrylic resins, inorganic silicate based resins, vinyl resins, particularly a vinyl chloride/vinyl acetate copolymer, and rosin.

Examples of pigments that may be used include titanium dioxide, cuprous oxide, iron oxide, talc, aluminum flakes, mica flakes, ferric oxide, cuprous thiocyanate, zinc oxide, cupric acetate meta-arsenate, zinc chromate, zinc dimethyl dithiocarbamate, zinc ethylene bis(dithiocarbamate) and zinc diethyl dithiocarbamate.

Examples of additives that may be incorporated into the coating composition include dehumidifiers, wetting/dispersing agents, anti-settling agents, anti-skinning agents, drying/curing agents, anti-marring agents and additives ordinarily employed in coating compositions as stabilizers and anti-foaming agents. Additionally, any antibiotic which is relatively insoluble in seawater can be used with an anti-fouling marine paint.

Methods of preparing marine anti-fouling paints are explained in detail in U.S. Pat. Nos. 4,678,512; 4,286,988; 4,675,051; 4,865,909; and 5,143,545.

The compositions of the present invention may also be used for providing antibacterial properties in cosmetics, to prevent spoiling of the product.

The compositions may further be used to provide an antibacterial effect to the mouth, teeth and gums, such as by incorporation in a toothpaste, mouthwash, or chewing gum. Taken together the present teachings portray a wide range of novel anti-adhesive agents isolated from organisms such as aquatic organisms and moss. The broad spectrum of the anti adhesion effects of these agents (e g inhibiting adhesion of gram positive and gram negative bacteria) together with their ability to effect the initial, vulnerable stages of microbial biofilm formation, makes these agents prime candidates as anti-biofilm agents. Moreover, the anti-adhesive agents described herein are clonable enabling modifications and mass production thereof. In addition their stability (i.e. resistance to environmental conditions) makes these agents suitable for a diverse array of applications.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology," John Wiley and Sons, Baltimore, Md. (1989); Perbal, "A Practical Guide to Molecular Cloning," John Wiley & Sons, New York (1988); Watson et al., "Recombinant DNA," Scientific American Books, New York; Birren et al. (eds) "Genome Analysis: A Laboratory Manual Series," Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook," Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology," W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1317, Academic Press; "PCR Protocols: A Guide To Methods And Applications," Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXAMPLES

Reference is now made to the following examples, which together with the above description, illustrate the invention in a non limiting fashion.

Example 1

MS/MS Analysis of an Active Fraction Extracted from *Aiptesia Anemone*

Figure 13:
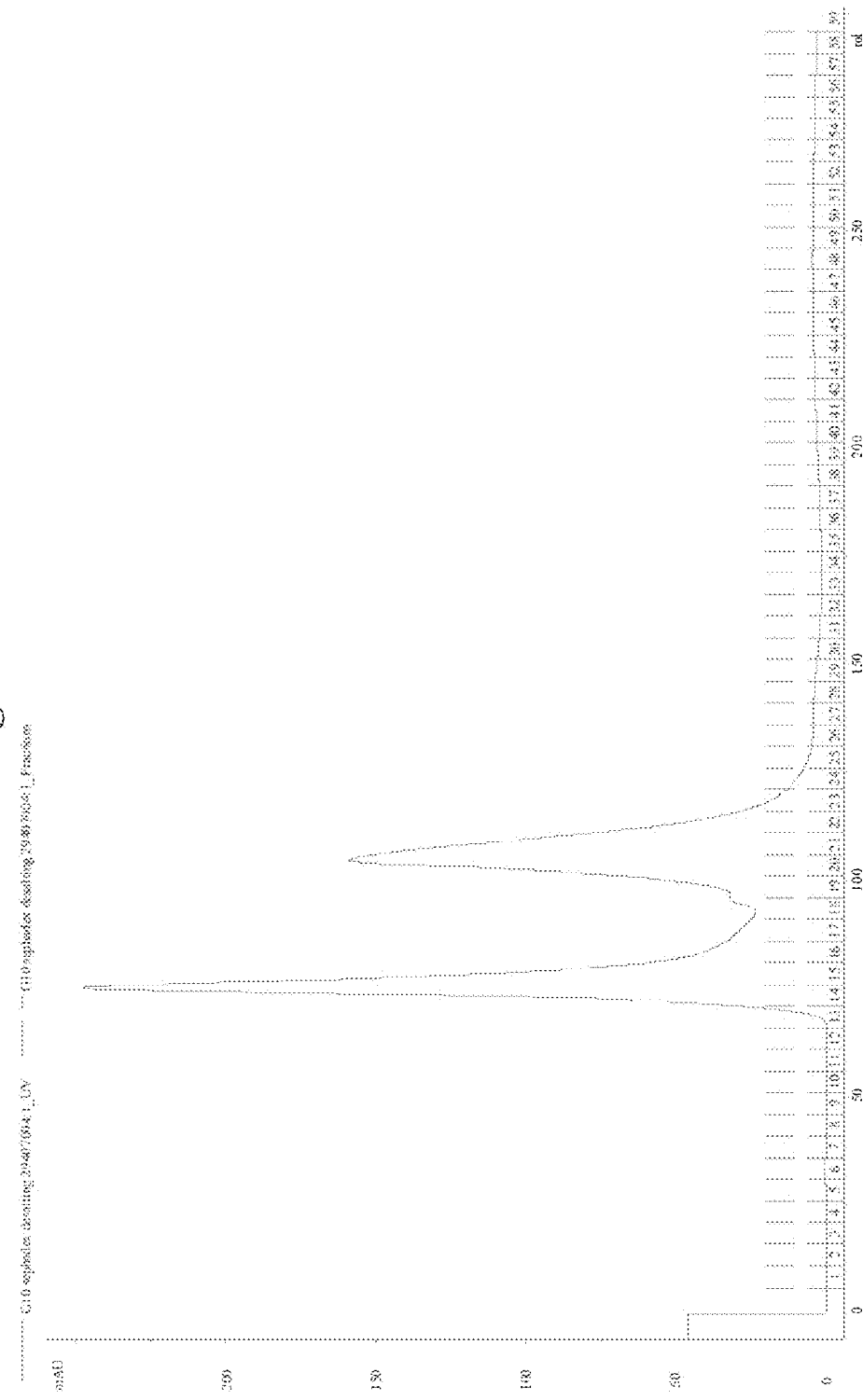
FIG. 13 shows fractions obtained by separation of crude extract of *Aiptasia pulchella* on Sephadex G-10 column.

Crude extract of *Aiptasia pulchella* (whole organism) was separated on Sephadex G-10 column resulted in 2 fractions, both exhibiting anti-adherence/biofilm formation activity (FIG. 13).

Figure 14:
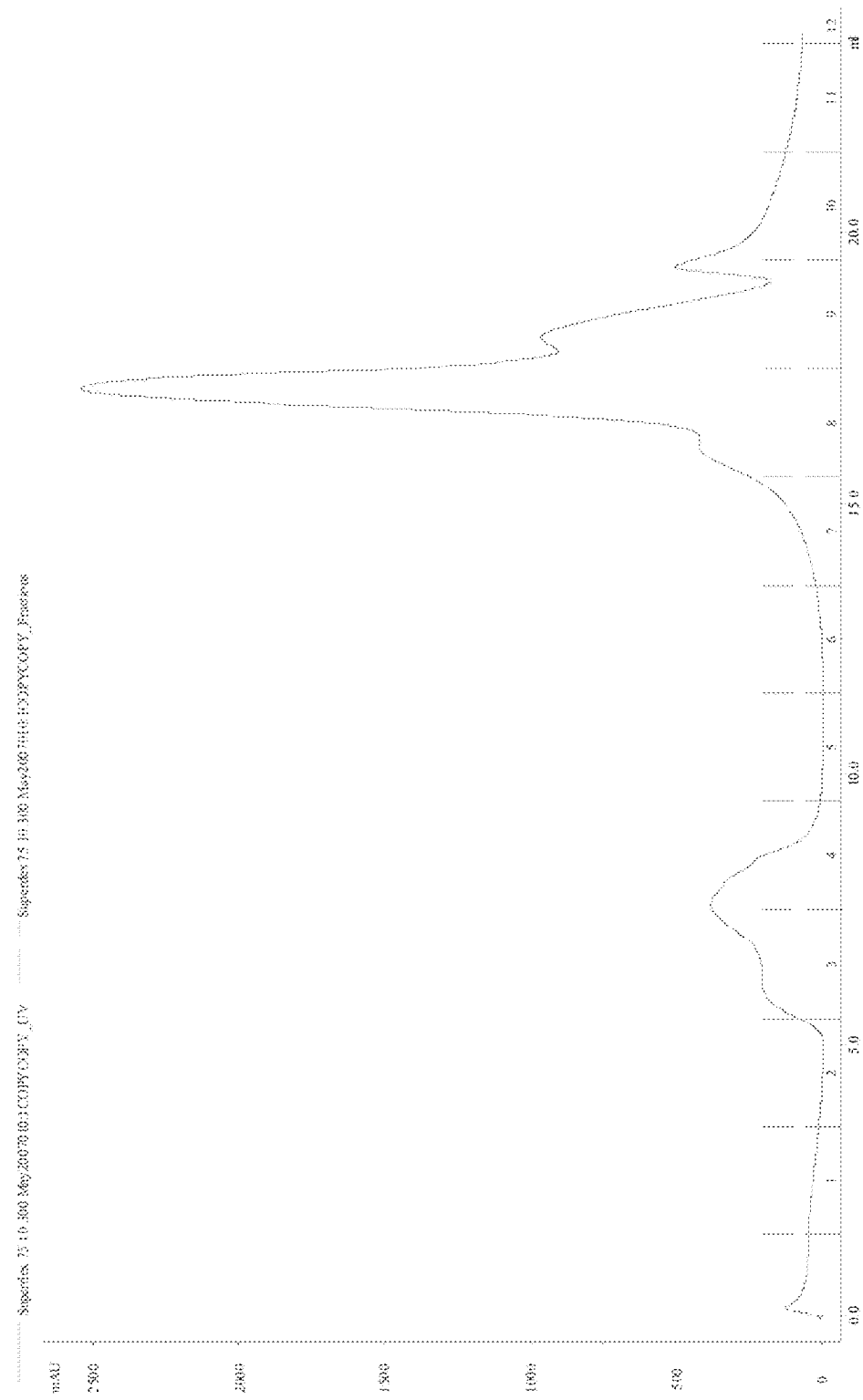
FIG. 14 shows peaks obtained by rechromatography of the high molecular weight fraction of FIG. 13.

Rechromatography of the high molecular fraction from Sephadex G-10 on Sephadex G-75 resulted in two main peaks representing high and low molecular fractions (FIG. 14).

Figure 15:
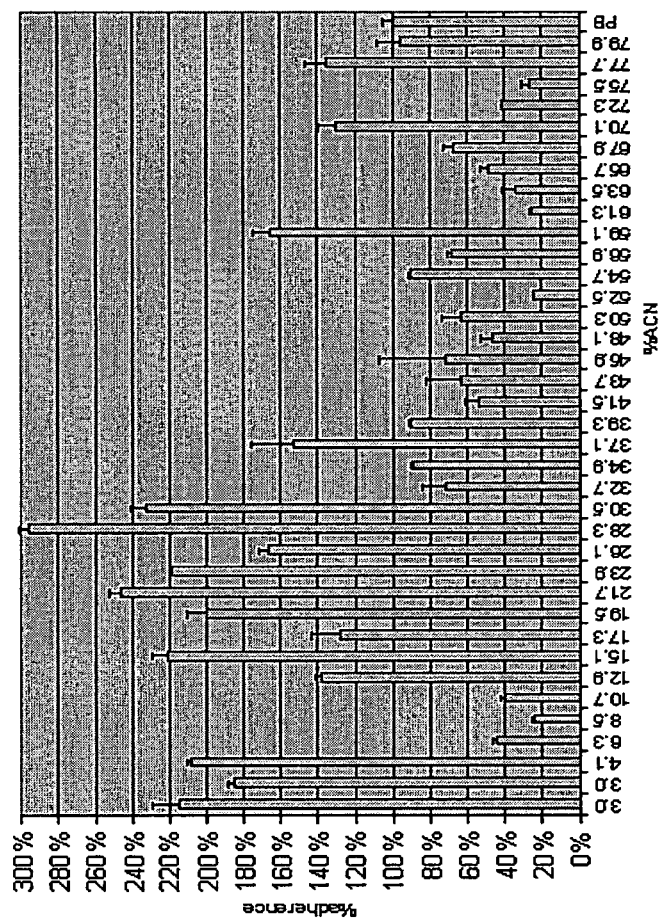
FIG. 15 shows fractions obtained by reversed phase high performance liquid chromatography (RP-HPLC) separation with c-18 column, of the low molecular fraction of FIG. 14.

Reversed phase high performance liquid chromatography (RP-HPLC) separation with c-18 column, of the low molecular fraction from the G-75 column, in linear gradients of acetonitrile (3-80% from 5 to 75 minutes) in 0.1% TFA at a flow rate of 2 ml/min, resulted in several active fractions as anti adhesive compounds on *Pseudomonas aeruginosa* ATCC 27853. Fractions were collected every 2 minutes (FIG. 15).

All active fractions where digested by trypsin, analyzed by LC-MS/MS on Qtof Premier (Waters) and on LTQ-Orbitrap (Thermo) and identified by Pep-Miner and Sequest software against the Eukaryotes part of the nr database. Active fraction eluted at 72.3% acetonitrile (marked in red arrow) was found to be similar to Equinatoxin 5 from *Actinia equine*.

Example 2

Identification of a Conserved Region of Anemone Cytotoxin

Purified template DNA was prepared from 25 mg of *Aiptasia pulchella* and *Anemonia viridans* using the wizard genomic DNA purification kit (Promega, USDA), according to the manufacturer's protocol for isolation of genomic DNA from animal tissue. PCR was carried out on 500 ng of purified template DNA from *Aiptasia pulchella* and *Anemonia viridans* using Reddy Mix PCR master mix (ABgene, UK), with the following protocol: 95° C.-5 min (95° C. 30 sec, 52° C. 30 sec and 72° C. 1 min)×35, 72° C. for 10 min.

Primers Eqt-F (GTR TCG ACA ACG AGT CRG G) (SEQ ID NO: 22) and Eqt-R252 (TGA CAT YCC ACC AGT TGC TG) (SEQ ID NO: 23) were added to the reaction mixture, to a final concentration of 0.51 µM each.

Positive PCR reactions which gave DNA amplicon of size of ~250 bp were sent for DNA sequencing.

A PCR amplicon from *Aiptasia pulchella* gave the following 265 bp sequence:

```
                                          (SEQ ID NO: 50)
GTGTCGCCAACGAGTCGGGATGCACTTGGGAAAAGCCAAATACATACTT

CTTCTCTGGTACTGAGGTATAAAGTGCCTCCCTCTAAAGCTTGAGAATA

AAAAAGCACTTTTGTACGGCCCACGTAAGACAACAGGGCCTGTTGCCAC

GGGAGCTGTTGGAGTGCTCACTTACAAAATGTTGTGCACCAATGAGACG

AACACTCTGGCTGTTCTTTTCAGTGTACCCTTCGACTACAACTTGTACA

GCAACTGGTGGAAATGTCAA
```

BLASTx comparison of the predicted amino acid sequence encoded by the above polynucleotide sequence to known protein sequences in the GeneBank provided the following results: Identities=54/88 (61%), Positives=62/88 (70%). To other anemone cytotoxins like: hemolytic toxin [*Actineria villosa*], PsTX-20A [*Phyllodiscus semoni*], cytolysin I precursor [*Sagartia rosea*] and equinatoxin IV precursor [*Actinia equina*]; (accession numbers: BAD74019.1, BAC45007.1, AAPO4347.1 and AF057028_1).

The relevant peptide sequence [FSVPFDYNLYSNWW] (SEQ ID NO: 51) appears m the Aiptasial sequence.

PCR amplicon from *Anemonia viridans* gave the following 254 bp sequence:

```
                                          (SEQ ID NO: 52)
TGTGTCGACAACGAGTCgGGCaagacgtGgaCCGCAntgaaCACATACT TCCGTTCTGGcACCTCTGATnTCrTCCTTCCCCATACAGTTCCACATGG

TAAGGCACTGCTCTACAACGGTCAGAAAGATCGTGGTCCAGTTGCGACT

GGCGtgGTTGGAGTACTTGCTTATGcCATGAGCgATGGAAACACCCtGG

CCGTTTTgTTCAGCrTTCCCTaTGACTATAACCtGTACAGCAACTGGTG

GAATGTCAA.
```

BLASTn comparison to known nucleotide sequences in the GeneBank gave similarities of 97%, 96% and 95% to Equinatoxins 5 [accession number: AEU51900], 4 [accession number: AF057028] and 2 [accession number: AEU41661], in correspondence.

Predicted amino acid sequence based on translation of the second positive ORF gave the following AA sequence:
CRQRVGMHLGKAKYILLLWY*GIKCLPLKLENKKA-LLYGPRKTTGPVATGAVGVLT YK MLCTNETNTLAV-LFSVPFDYNLYSNWWKCQ (SEQ ID NOS 53 and 62, respectively, in order of appearance).

Example 3

Comparison of Activity of Synthetic Peptides

Peptides listed below were synthesized using solid-phase methods and purification to 90% scale was performed by Peptron Inc. (Taejeon, Korea).

The peptides were dissolved using 20 μl dimethyl sulfoxide (DMSO) and diluted in double distilled-water to a concentration of 5 mg/ml. Further dilutions were performed in phosphate buffered saline (PBS).

The activities of the following synthetic peptides were studied on a clinical isolate of *Acinetobacter Baumannii* and *Pseudomonas aeruginosa* ATCC 27853 at peptide concentrations ranging from 500-0.5 μg/ml. Peptides diluted to appropriate concentrations were incubated with the bacteria for 24-48 hours.

For bacterial adherence bioassays, biofilms were grown in 96-well round-bottom polystyrene plates. Briefly, 180 μl of overnight cultures were added to wells supplemented with 20 μl of appropriate peptide diluted in PBS. After 24 h of incubation at 37° C., each well was washed with water and was stained with 250 μl of crystal violet solution. The dye was then removed by thorough washing with water. For quantification of attached cells, crystal violet was solubilized in 250 μl of 1% sodium dodecyl sulfate (SDS) and the absorbance was measured at 595 nm.

```
CMFSVPFDYNWYSNWWC        (SEQ ID NO: 32)
                         AbacZ-17C

Ac-MFSVPFDYNWYSNWW-NH2   (SEQ ID NO: 54)
                         AbacZ-15

CFSVPFDYNWYSNWWC         (SEQ ID NO: 55)
                         AbacZ-16C

FDYNWY                   (SEQ ID NO: 5)
                         AbacZ-6

CFDYNWYC                 (SEQ ID NO: 56)
                         AbacZ-8C
```

Figure 7:
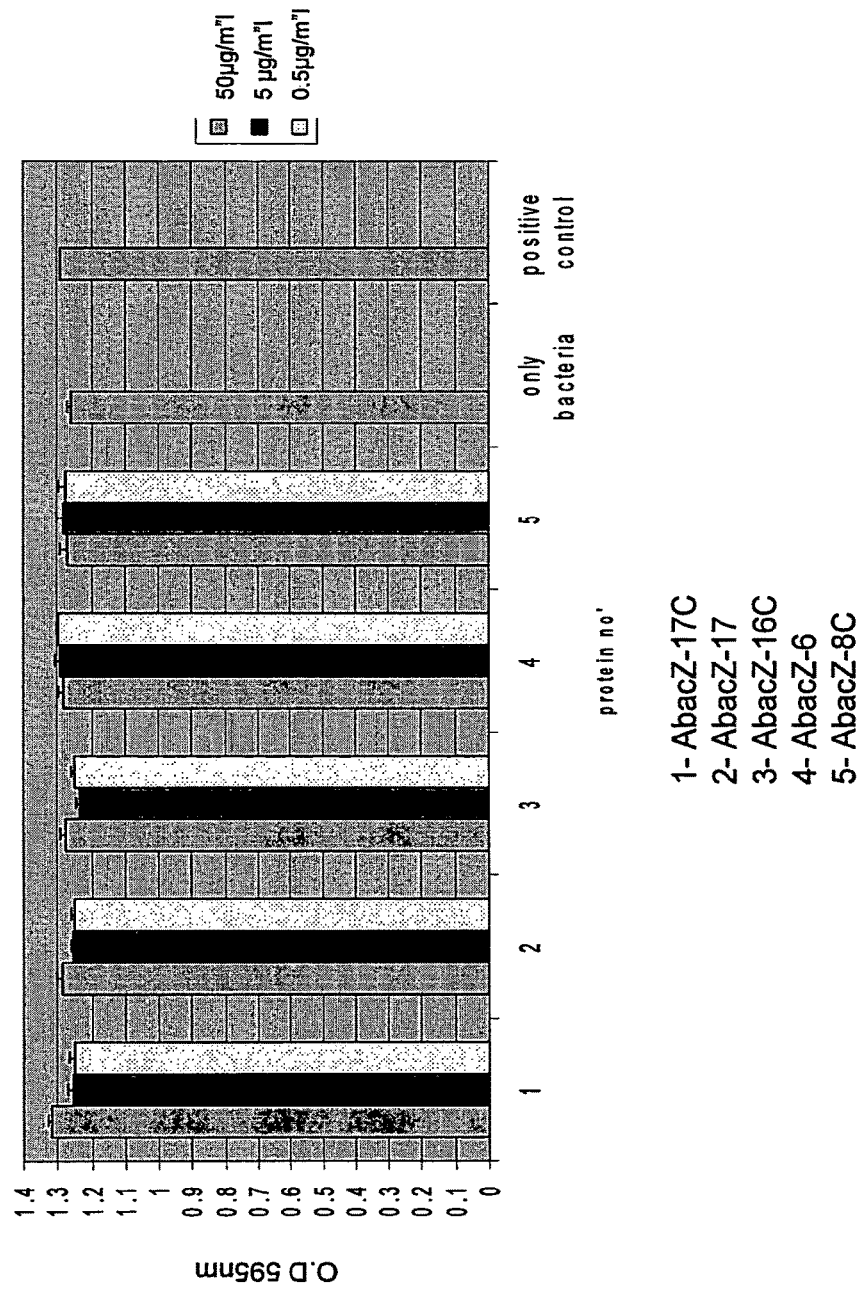
FIG. 7 is a bar chart showing the effects of different concentrations of synthetic proteins on growth of a clinical isolate of *Acinetobacter Baumannii* over 24 hours; No bactericidal or bacteriostatic effect.
Figure 8:
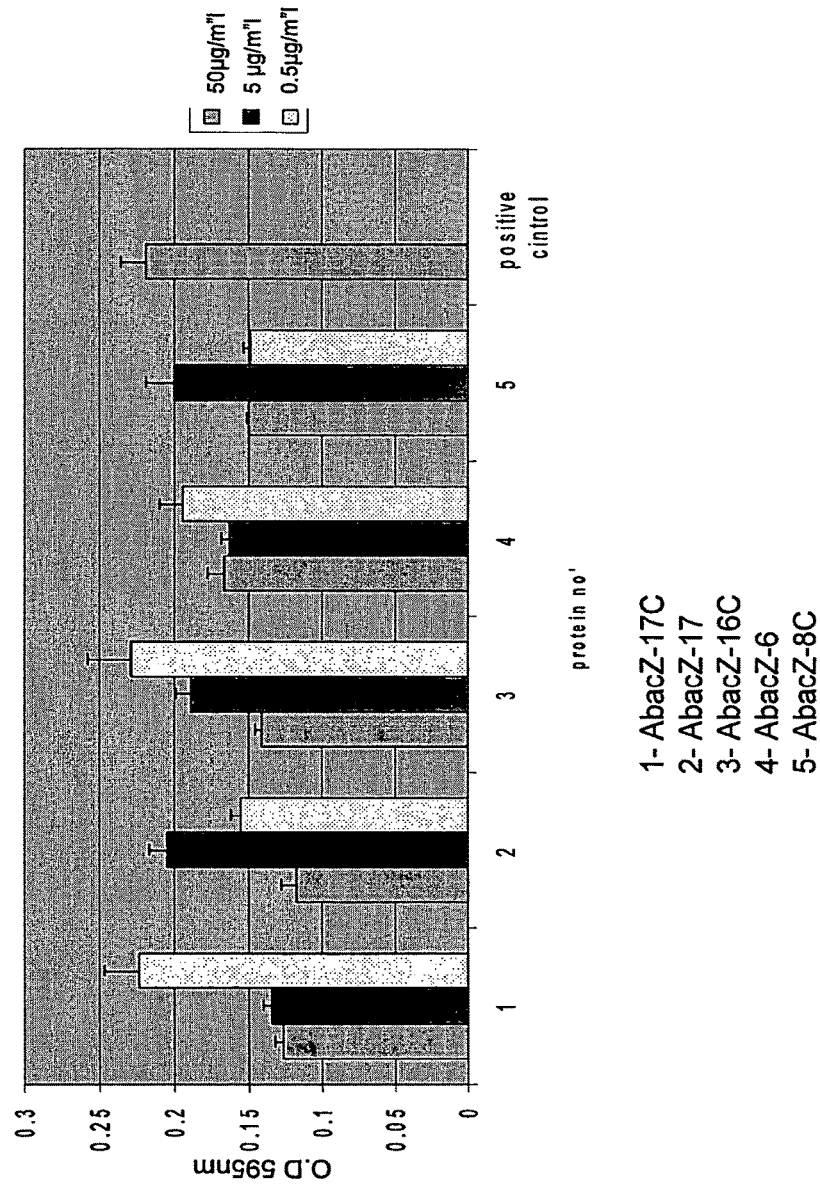
FIG. 8 is a bar chart showing the effects of different concentrations of synthetic proteins on biofilm formation by a clinical isolate of *Acinetobacter Baumannii* over 24 hours.
Figure 9:
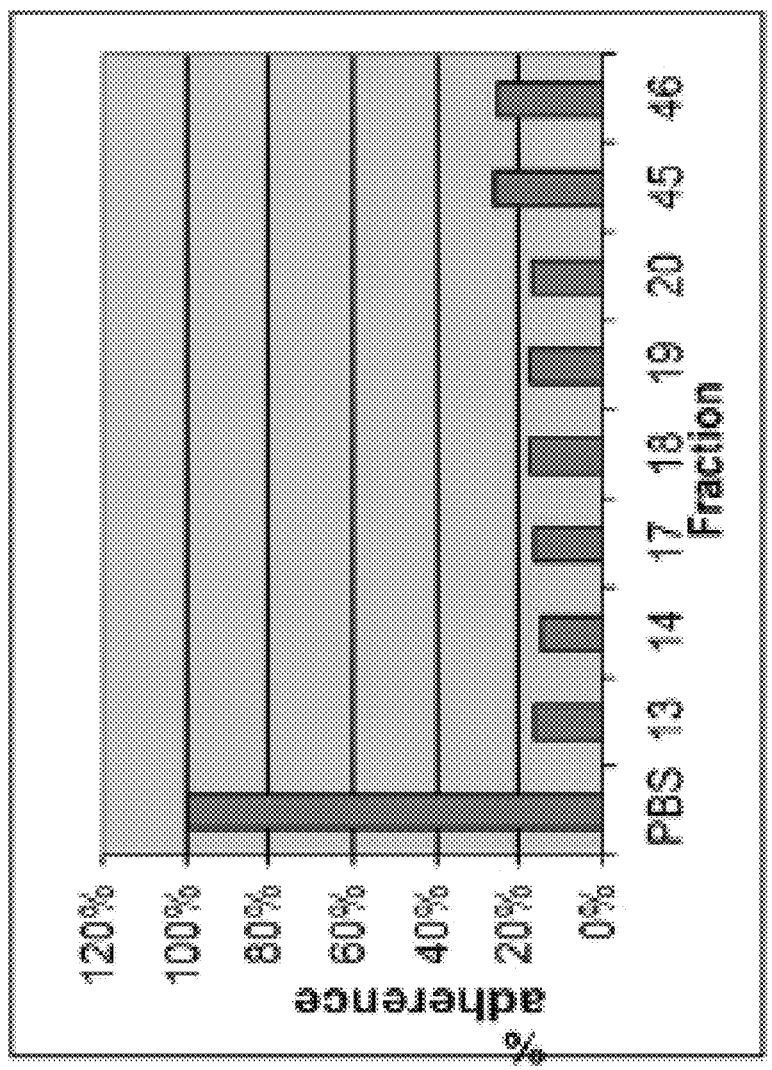
FIG. 9 is a bar chart showing the effects of selected tentacular fractions from *Actinia equina* on biofilm formation by *Acinetobacter baumannii*, with PBS as a positive control.
Figure 10:
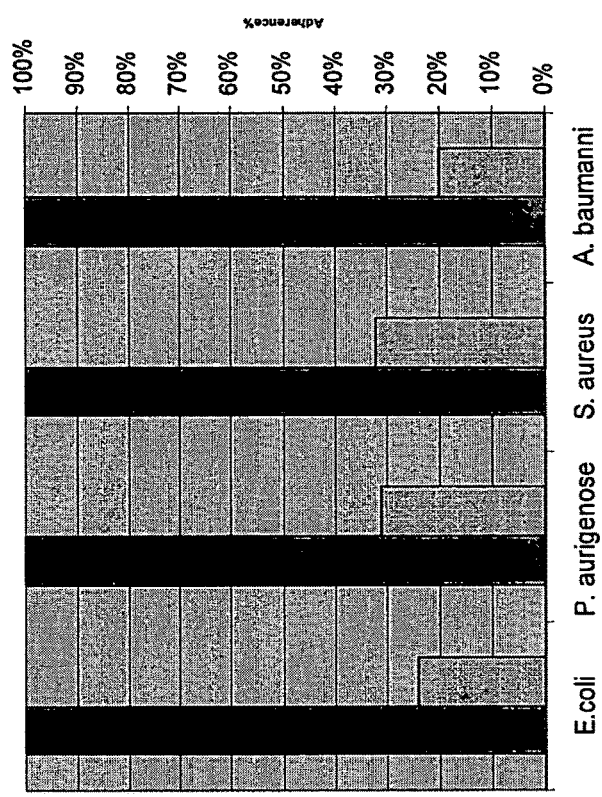
FIG. 10 is a bar chart showing the effects of fraction 13 on biofilm formation by various gram positive and gram negative bacteris.
Figure 11:
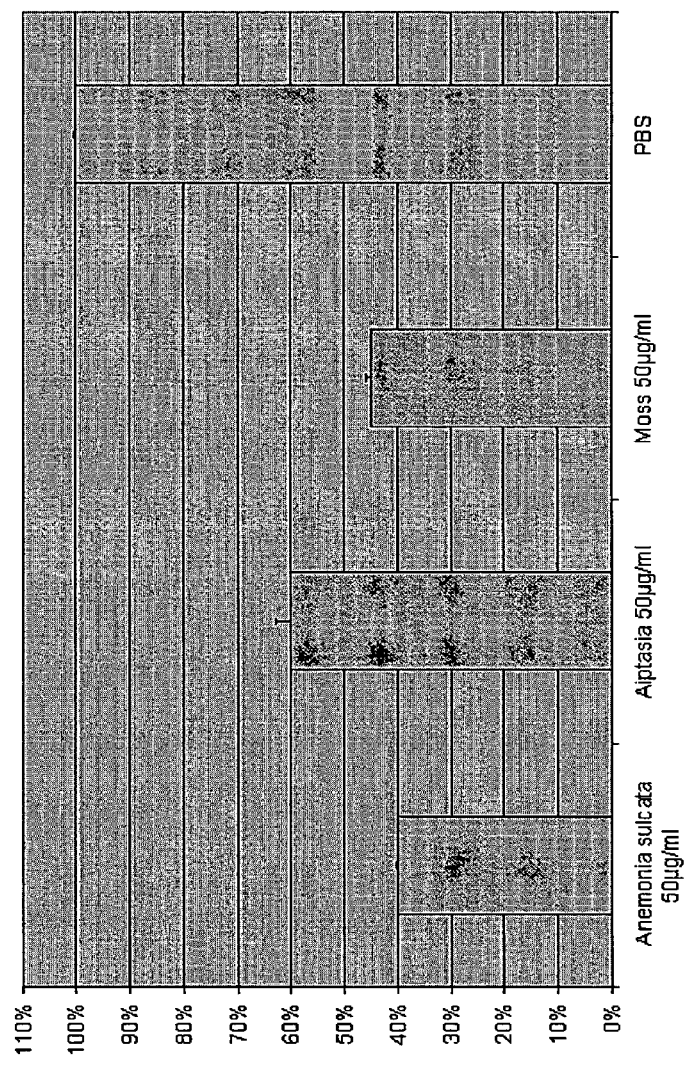
FIG. 11 is a bar chart showing the effects of crude extracts from *Anemonia, Aiptasia* and *Physcomitrella* (Moss) on *Pseudomonas aeruginosa* in protein concentration of 50 µg/ml.
Figure 12:
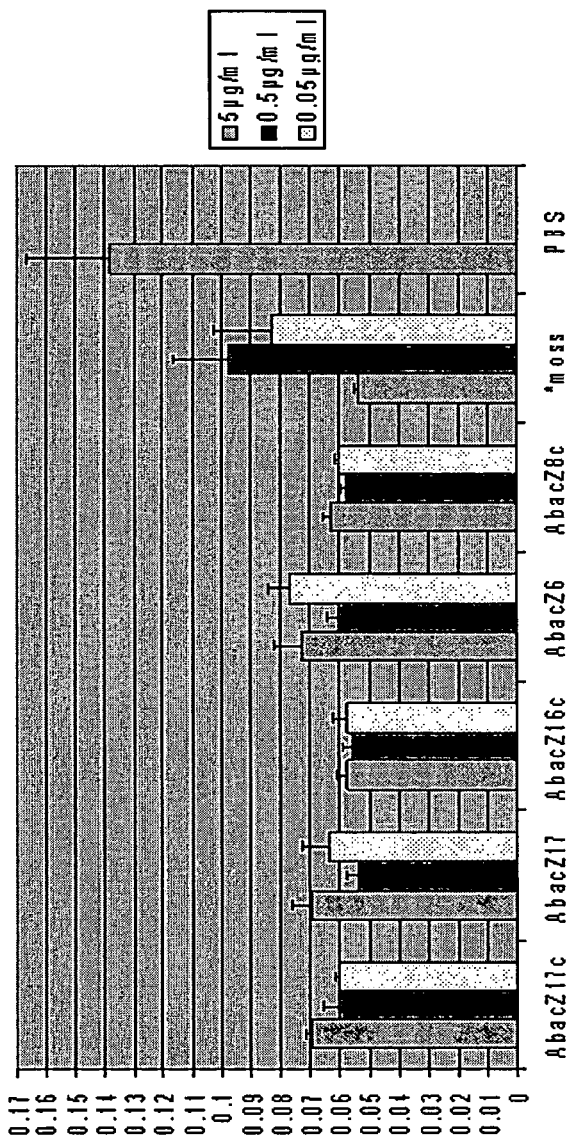
FIG. 12 is a bar chart showing the effects of five synthetic peptides and crude material from the moss of *Physcomitrella patens;*

Results are shown in FIGS. 1 to 12. As seen in FIGS. 5 and 7, the peptides did not kill or inhibit growth of bacteria. FIGS. 6, 8 and 10 to 12, demonstrate that the peptides prevented the formation of biofilms.

Example 4

Identification of Preferred Peptides

In order to identify the most active cyclic peptides according to the present invention, a manual Parallel Peptide synthesizer with peptide purifier is used to produce peptides which differ from each other in length and cyclization strategy. Each peptide is screened for anti-30 adhesive activity in microplate and flow cell assays, and selection of highly active peptides is performed. Computerized modeling of several versions of peptide is used to optimize selection of the active compounds.

For more sensitive screening the bioassay is scaled up using the BacTiter-Glo microbial cell viability Assay of Promega, USA. This method uses more sensitive spectrometric technique based on luminescence.

Figure 16A:
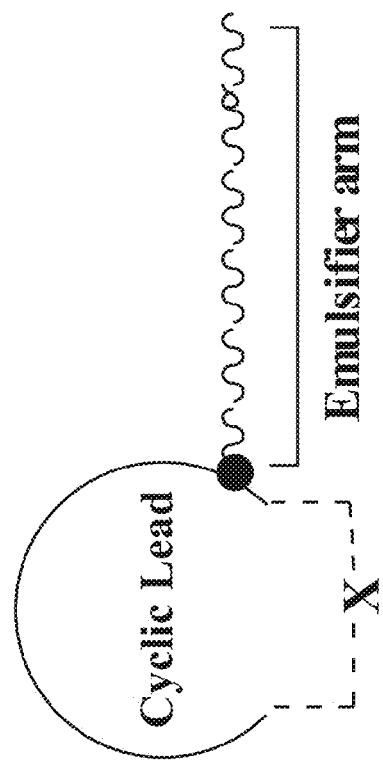
FIGS. 16A-B show the general structure of a cyclic lead with emulsifier arm of a peptide according to the principles of the present invention.
Figure 16B:
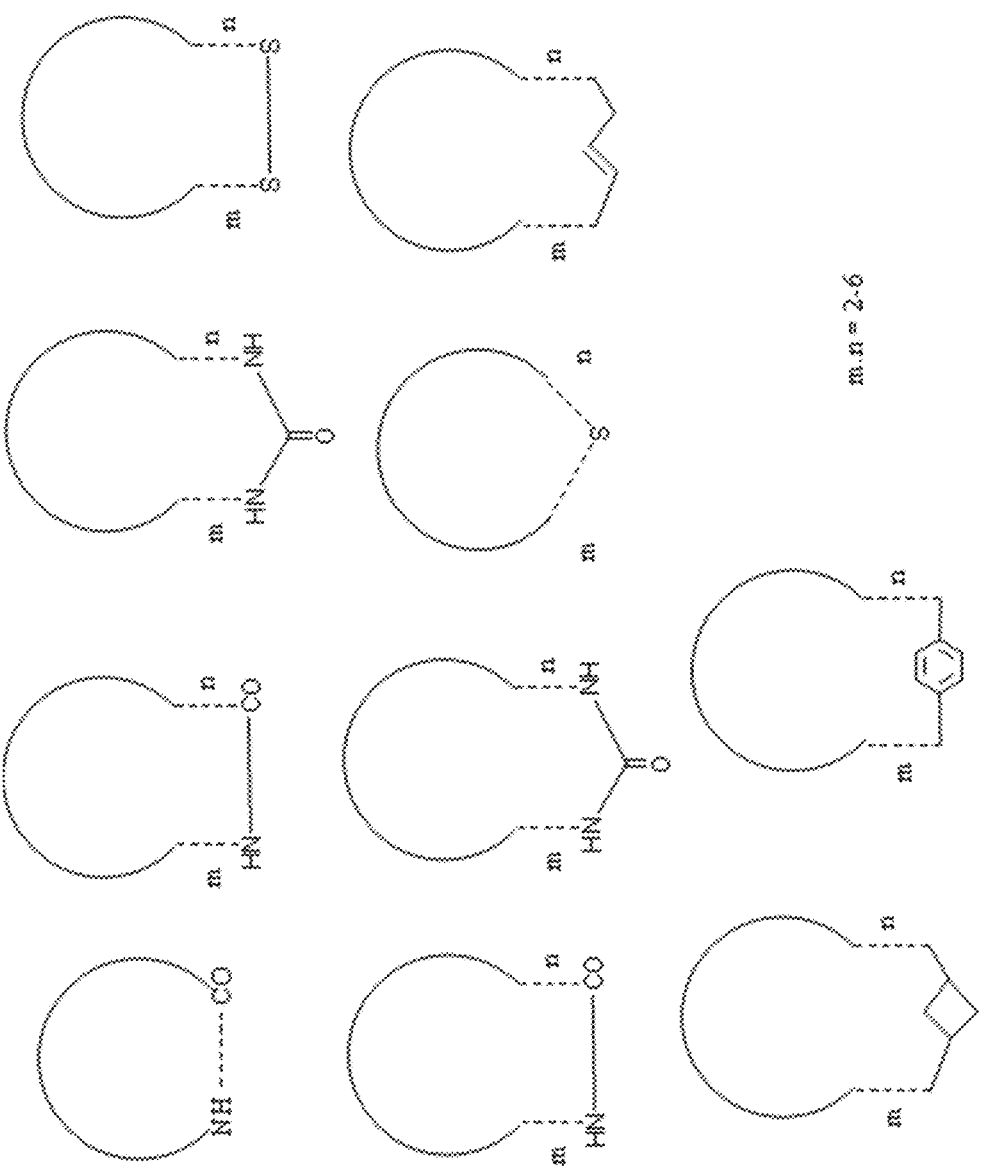

Various cyclization strategies are used to obtain optimized cyclic peptide from linear analog with satisfactory bioactivity. FIG. 16A shows the generalized structure of the cyclic lead with emulsifier arm. The linear analog is a 14mer peptide with hydrophobic core (baa) that is defined as a pharmaeophore. Cyclic leads are prepared, preserving this pharmacophore and an emulsifying arm (hydrophobic moiety) such as polyethylene, polypropylene, Teflon etc. is then added to provide absorbing capabilities to a hydrophobic polymeric surface (FIG. 16B).

Epitope mapping, escanning and Cycloscan methodologies are used for revealing shorter, more cost-effective, peptides possessing the desired biological activity.

The cyclic lead is prepared using 9H-fluoren-9-yl-methoxycarbonyl solid phase peptide synthesis (Fmoc SPPS).

Figure 17:
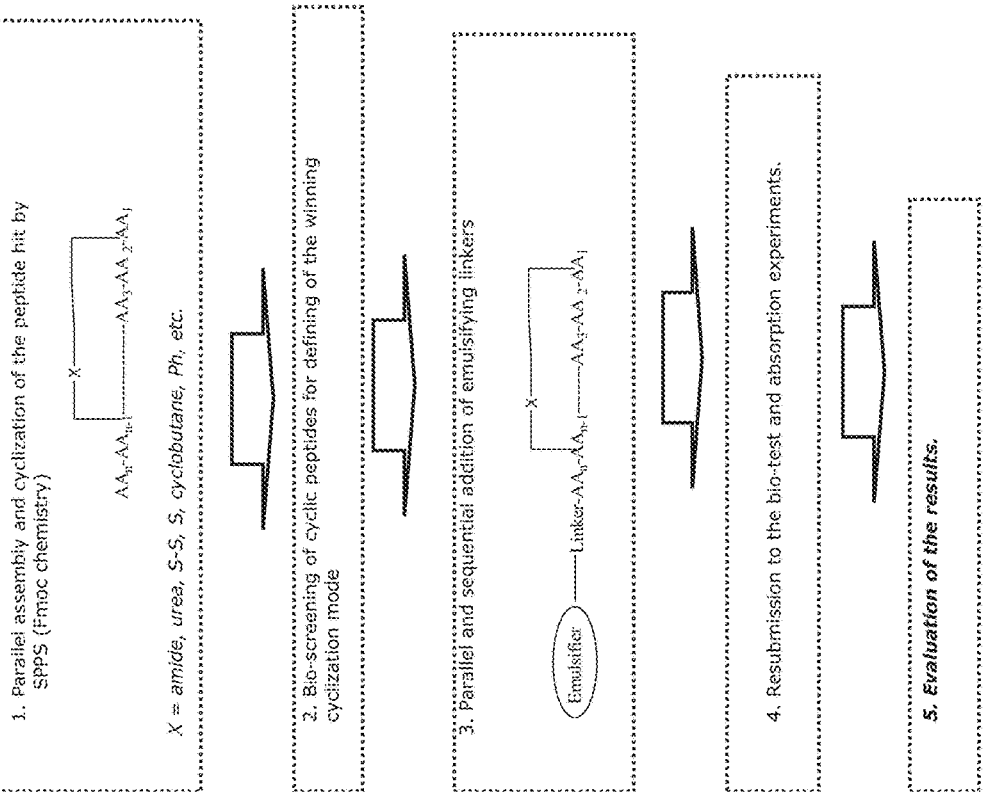
FIG. 17 is a flow chart showing development of a cyclic peptide lead with emulsifying arm.

According to a representative procedure, as shown in FIG. 17, the first protected amino acid is condensed with chlorotityl (Cl-Trt) resin using N,N-diisopropylethylamine (DIEA) in dichloromethane (DCM) or with Rink Amide using O-Benzotriazole-N,N,N',N'-tetramethyl-uronium-hexafluoro-phosphate (HBTU) as coupling reagent.

The next couplings are performed using a standard Fmoc protocol with 2-(1H-7-Azabenzotriazol-1-yl)-1,1,3,3-tetramethyl uronium hexafluorophosphate Methanaminium (HATU) or benzotriazol-1-yl-oxytripyrrolidinophosphonium hexafluorophosphate (PyBoP), DIEA in N-methyl-2-pyrrolidinone (NMP). The allyloxycarbonyl (alloc) groups are deprotected by Pd-triphenylphosphine (Tetrakis) using acetyl hydroxide/N-methyl maleimide/diethene chloride (AcOH/NMM/DCE) cocktail.

The cyclization step is carried out as a standard coupling reaction (in the case of formation of an amide bond) or by bubbling oxygen (in the case of formation of a disulfide bridge). Other types of cyclizations as known in the art may also be performed.

The peptides are cleaved from the resin by treatment with trifluoroacetic acid:dichloromethane:tri-iso-propylsilane (TFA:DCM:TIS), 1:98:1 in the presence of 1,2-ethanedithiol for 30 min in case of the Cl-Trt resin, and in the presence of 95% TFA, TIS and $H_2O$ in the case of Rink Amide.

The crude product in the solution (AcOH/$H_2O$ 1:1) is purified by preparative HPLC or MPLC to afford pure cyclic peptide. The purity is determined by analytical HPLC. The structures are confirmed by LC-MS and AA analysis.

The next stage involves linkage of the hydrophobic arm for introducing absorbing properties to the cyclic peptide lead. This arm is linked using standard SPPS protocol.

FIG. 17 shows a flowchart outlining the process for development of a cyclic peptide lead with an emulsifying arm.

Example 5

Treatment of Water or Fluid Medium

The above peptides and/or compositions and/or organisms may optionally and preferably be used to treat water and/or a fluid medium, or a system or apparatus containing such, including but not limited to a reverse osmosis filter and/or filtration apparatus or system.

The effect of Actiniaria extracts on biofilm formation using polyamide coupons in a flow cell without filtration is tested as follows. The effect of biofilm growth is analyzed in a flowcell dedicated for confocal microscopy on a similar polyamide surface as an RO (reverse osmosis) active layer. A dual channel flowcell (FC 270, Biosurface Technologies, Montana, USA) is operated with both model strains and real microbial inoculum taken from reverse osmosis (RO) membrane coupon located in selected places on the Mediterranean sea supplemented with different concentrations (from nanograms to micrograms per ml) of the extracts. The flow regime in the flowcells is laminar and similar to a typical RO operational flow conditions. For the model strains, seawater synthetic media is determined (see (Fritzmann et al., 2007: Fritzmann, C., Lowenberg, J., Wintgens, T., and Melin, T. (2007) State-of-the-art of reverse osmosis desalination. Desalination 216: 1-76) and IDE reports ide-tech.tech.com/) and are used for cell attachment biofilm growth experiments. For the microbial consortium being isolated from the desalination plant in Palmachim, real seawater is used as a media for microbial attachment and biofilm growth experiments. Model strains to be used are *Vibrio fisheri* and *Caulobacter crescentus*. In the dual channel flowcell, one channel is supplemented with an extract and the other serves as a control with only the solvent being added to the media (for example, when the extract is dissolved in ethanol).

The flowcell biofilms are microscopically analyzed at different time points (up to 14 days of experiment) when viable cells, dead cells and Extra cellular polymeric substances (EPS) are stained with fluorescent probes (different flourescent labeled lectins are used for probing different polysacharide constitutents in the EPS) and visualized with laser scanning confocal microscopy (LSCM). Microscopic analysis is performed using image processing analysis softwares such as Imaris bitplane and COMSTAT (Heydorn et al., 2002: Ersboll, B., Kato, J., Hentzer, M., Parsek, M. R., Tolker-Nielsen, T. et al. (2002) Statistical analysis of *Pseudomonas aeruginosa* biofilm development: impact of mutations in genes involved in twitching motility, cell-to-cell signaling, and stationary-phase sigma factor expression. Applied and Environmental Microbiology 68: 2008-2017).

Calcium, which has significant effect on the adhesiveness and the compactness of the biofilm is also monitored and visualized with LSCM using Calcium specific fluorochromes such as Fura-2 (Grynkiewicz et al., 1985: Grynkiewicz, G., Poenie, M., and Tsien, R. Y. (1985) A new generation of Ca2+ indicators with greatly improved fluorescence properties, Journal of Biological Chemistry 260: 3440-3450; Neu et al., 2002: Neu, T. R., Kuhlicke, U., and Lawrence, J. R. (2002) Assessment of Fluorochromes for Two-Photon Laser Scanning Microscopy of Biofilms, Applied and Environmental Microbiology 68: 901-909).

Antifouling properties are also examined by analyzing the adherence of different types of EPC/bacteria with QCM-D surface-modified crystals covalently bonded to different peptides.

QCM-D employs an ultra-sensitive mass sensor (silica-coated quartz crystal) housed inside a flow cell with a well-defined geometry and hydrodynamic characteristics, a design that allows real-time monitoring of mass adsorption with no required labeling. The piezoelectric quartz crystal oscillates laterally with an amplitude of 1-2 nm when a voltage is applied to the electrodes affixed to the quartz crystal. As deposition (adsorption) occurs on the crystal surface, it leads to a shift in the vibrational frequency of the crystal. In addition to monitoring the frequency shift to determine the adsorbed mass, thickness and structural conformation of the adsorbed layer can be extracted by simultaneous monitoring of the energy of dissipation, which is the sum of all energy losses within the system per oscillation cycle. Intriguingly, in addition to measuring the adsorption and adherence of the different types of EPS (i.e., changes in polysaccharides/protein contents) under different environmental conditions (i.e., changes in divalent cation concentrations), QCM-D can also reveal the visco-elastic properties, conformational changes, and thickness of the precipitated nano-layer.

Example 6

Effect of Active Peptides on Reverse Osmosis Biofouling Under Desalination Conditions The effect of Actiniaria extracts on reverse osmosis biofouling under desalination conditions is determined Two RO (reverse osmosis) bench-scale units are operated for desalination of seawater, and biofouling experiments with both candidate model strains and microbial consortium isolated from the GES desalination plant (as mentioned above) are conducted both in a synthetic seawater media and a real seawater. Commercialized flat-sheet membranes SW-30 of Dow-Filmtec are used for these biofouling experiments. Specific measures of process conditions are obtained: permeate flux, total organic carbon (TOC), oxygen concentrations in the permeate and in the brine solution, oxygen uptake rate, and the rejection of different ions and cations by the membrane. Different biofilm components are analyzed: Chemical analysis of the biofouling layer will include characterization of proteins, carbohydrates, lipids, and DNA. Microscopic observation and analysis is performed as mentioned above.

While the invention has been described with respect to a limited number of embodiments, it will be appreciated that many variations, modifications and other applications of the invention may be made.

The invention claimed is:

1. A cyclic peptide comprising one of the sequences YDYNWY (SEQ ID NO: 1), YDYNLY (SEQ ID NO: 2), FDYNFY (SEQ ID NO: 3), FDYNLY (SEQ ID NO: 4), WDYNLY (SEQ ID NO: 8), FDYNWY (SEQ ID NO: 5), YDWNLY (SEQ ID NO: 6), and YDWHLY (SEQ ID NO: 7), wherein the peptide is cyclized by a covalent bond, and wherein the total length of the peptide is 50 amino acids or less.

2. The peptide according to claim 1, wherein the total length is 40 amino acids or less.

3. The peptide according to claim 1, wherein the total length is 30 amino acids or less.

4. The peptide according to claim 1, comprising the sequence YDYNWY (SEQ ID NO: 1), which is cyclic and wherein the total length is 30 amino acids or less.

5. The peptide according to claim 1, wherein the peptide is cyclized by an amide bond or a disulfide bridge.

* * * * *